United States Patent [19]
Romley et al.

[11] Patent Number: 5,911,702
[45] Date of Patent: Jun. 15, 1999

[54] METHODS AND DEVICES FOR CANNULATING A PATIENT'S BLOOD VESSEL

[75] Inventors: Richard M. Romley, Alameda; Brian S. Donlon, Los Altos Hills; Timothy J. Corvi, Belmont; Sylvia W. Fan, San Francisco; Jan Komtebedde, Cupertino; Keke J. Lepulu; Sylvester B. Lucatero, both of Sunnyvale, all of Calif.

[73] Assignee: Heartport, Inc., Redwood City, Calif.

[21] Appl. No.: 08/965,273

[22] Filed: Nov. 6, 1997

[51] Int. Cl.⁶ .......................... A61M 29/02; A61M 29/00
[52] U.S. Cl. .............................. 604/53; 604/96; 604/171; 604/280
[58] Field of Search .................................. 604/19, 27, 28, 604/49, 51–53, 93, 96–99, 104–109, 158, 164, 171, 239, 272, 280, 282, 915, 921, 286; 623/900

[56] References Cited

U.S. PATENT DOCUMENTS

| | | |
|---|---|---|
| Re. 35,352 | 10/1996 | Peters . |
| 3,460,541 | 8/1969 | Doherty . |
| 3,598,127 | 8/1971 | Wepsic . |
| 3,616,799 | 11/1971 | Sparks . |
| 3,877,429 | 4/1975 | Rasumoff . |
| 4,184,497 | 1/1980 | Kolff et al. .............................. 604/280 |
| 4,309,994 | 1/1982 | Grunwald . |
| 4,327,735 | 5/1982 | Hampson . |
| 4,401,433 | 8/1983 | Luther . |
| 4,411,655 | 10/1983 | Schreck . |
| 4,498,902 | 2/1985 | Ash et al. . |
| 4,536,176 | 8/1985 | Gustavsson et al. . |
| 4,540,404 | 9/1985 | Wolvek . |
| 4,564,014 | 1/1986 | Fogarty et al. . |
| 4,573,981 | 3/1986 | McFarlane . |
| 4,601,713 | 7/1986 | Fuqua . |
| 4,685,447 | 8/1987 | Iversen et al. ............................. 604/96 |

(List continued on next page.)

FOREIGN PATENT DOCUMENTS

| | | |
|---|---|---|
| 1001034 | 12/1976 | Canada . |
| 0 086 338 | 8/1983 | European Pat. Off. . |
| 0 218 275 | 4/1987 | European Pat. Off. . |
| 1.211.941 | 10/1959 | France . |
| WO 96/22122 | 7/1996 | WIPO . |

OTHER PUBLICATIONS

Benedict et al., "Acute Aortic Dissection During Cardiopulmonary Bypass," *Arch Surg*, 1974;108:810–813.

Blackshear et al., "Some Mechanical Effects that Influence Hemolysis," *Trans Amer Soc Artif Int Organs*, 1965;11:112–117.

Brodman et al., "A Comparison of Flow Gradients across Disposable Arterial Perfusion Cannulas," *Ann Thorac Surg*, 1985;39(3):225–233.

Guidoin et al., "New Frontiers of Vascular Grafting," *Int Surg*, 1988;73:241–249.

Hwang et al., "Hydraulic Studies of Aortic Cannulation Return Nozzles," *Trans Amer Soc Artif Int Organs*, 1975;21:234–241.

(List continued on next page.)

*Primary Examiner*—Wynn Wood Coggins
*Assistant Examiner*—Sharon Finkel
*Attorney, Agent, or Firm*—Jens E. Hoekendijk; Jeffry J. Grainger

[57] ABSTRACT

A method and device for introduction of a catheter and/or delivering a fluid, such as oxygenated blood, to a patient's vascular system includes a cannula having an expandable portion. The expandable portion is movable from a collapsed position to an expanded position. The expandable portion is inserted into the patient in the collapsed position which facilitates introduction and advancement of the cannula through the patient's blood vessel. After introduction into the patient, the expandable portion is moved to the expanded position. The expandable portion protects the blood vessel against fluid forces when flowing a fluid through the cannula and protects the vessel from contact with the catheter advanced through the cannula.

25 Claims, 22 Drawing Sheets

U.S. PATENT DOCUMENTS

| | | |
|---|---|---|
| 4,710,181 | 12/1987 | Fuqua . |
| 4,738,666 | 4/1988 | Fuqua . |
| 4,921,484 | 5/1990 | Hillstead ................................. 604/104 |
| 5,037,404 | 8/1991 | Gold et al. ............................... 604/282 |
| 5,078,681 | 1/1992 | Kawashima . |
| 5,176,659 | 1/1993 | Mancini . |
| 5,176,692 | 1/1993 | Wilk et al. ................................ 604/96 |
| 5,304,183 | 4/1994 | Gourlay et al. . |
| 5,312,344 | 5/1994 | Grinfeld et al. . |
| 5,330,498 | 7/1994 | Hill . |
| 5,352,236 | 10/1994 | Jung et al. ................................ 604/96 |
| 5,370,685 | 12/1994 | Stevens . |
| 5,411,552 | 5/1995 | Andersen et al. . |
| 5,415,666 | 5/1995 | Gourlay et al. . |
| 5,425,705 | 6/1995 | Evard et al. . |
| 5,452,733 | 9/1995 | Sterman et al. . |
| 5,458,574 | 10/1995 | Machold et al. . |
| 5,472,418 | 12/1995 | Palestrant . |
| 5,478,309 | 12/1995 | Sweezer et al. . |
| 5,499,996 | 3/1996 | Hill . |
| 5,501,698 | 3/1996 | Roth et al. . |
| 5,522,838 | 6/1996 | Hill . |
| 5,536,251 | 7/1996 | Evard et al. . |
| 5,545,214 | 8/1996 | Stevens . |
| 5,556,412 | 9/1996 | Hill . |
| 5,558,644 | 9/1996 | Boyd et al. . |
| 5,569,274 | 10/1996 | Rapacki et al. . |
| 5,571,215 | 11/1996 | Sterman et al. . |
| 5,584,803 | 12/1996 | Stevens et al. . |
| 5,588,949 | 12/1996 | Taylor et al. . |
| 5,601,576 | 2/1997 | Garrison . |
| 5,613,937 | 3/1997 | Garrison et al. . |
| 5,616,137 | 4/1997 | Lindsay . |
| 5,618,267 | 4/1997 | Palestrant . |
| 5,618,306 | 4/1997 | Roth et al. . |
| 5,618,307 | 4/1997 | Donlon et al. . |
| 5,626,607 | 5/1997 | Malecki et al. . |
| 5,669,924 | 9/1997 | Shaknovich ............................. 604/101 |
| 5,674,240 | 10/1997 | Bonutti et al. .......................... 604/282 |
| 5,682,906 | 11/1997 | Sterman et al. . |
| 5,695,457 | 12/1997 | St. Goar et al. . |
| 5,702,368 | 12/1997 | Stevens et al. . |
| 5,709,335 | 1/1998 | Heck . |
| 5,718,725 | 2/1998 | Sterman et al. . |
| 5,741,271 | 4/1998 | Nakao et al. ........................... 604/280 |

OTHER PUBLICATIONS

Kay et al., "Retrograde Ilioaortic Dissection, A Complication of Common Femoral Artery Perfusion during Open Heart Surgery," *Am J Surg*, 1966;3:464–468.

King et al., "Designing Polyester Vascular Prostheses for the Future," *Med Progo Technol*, 1983;9;217–226.

Matar and Ross, Traumatic Arterial Dissection in Open–heart Surgery, *Thorax*, 1967;22:82–87.

Pfaender et al., "Hemodynamics in the Extracorporeal Aortic Cannula; review of Factors Affecting Choice of the Appropriate Size," *The Journal of Extra–corporeal Technology*, 1981;13(4):224–232.

Salerno et al., "Arch Versus Femoral Arteyr Perfusion During Cadiopulmonary Bypass," *J Thorac Card Surg*, 1978;76(5):681–684.

Vathayanon et al., "Retrograde Aortic Dissection During Cardiopulmonary Bypass," *Ann Thorac Surg*, 1967;4(5):451–453.

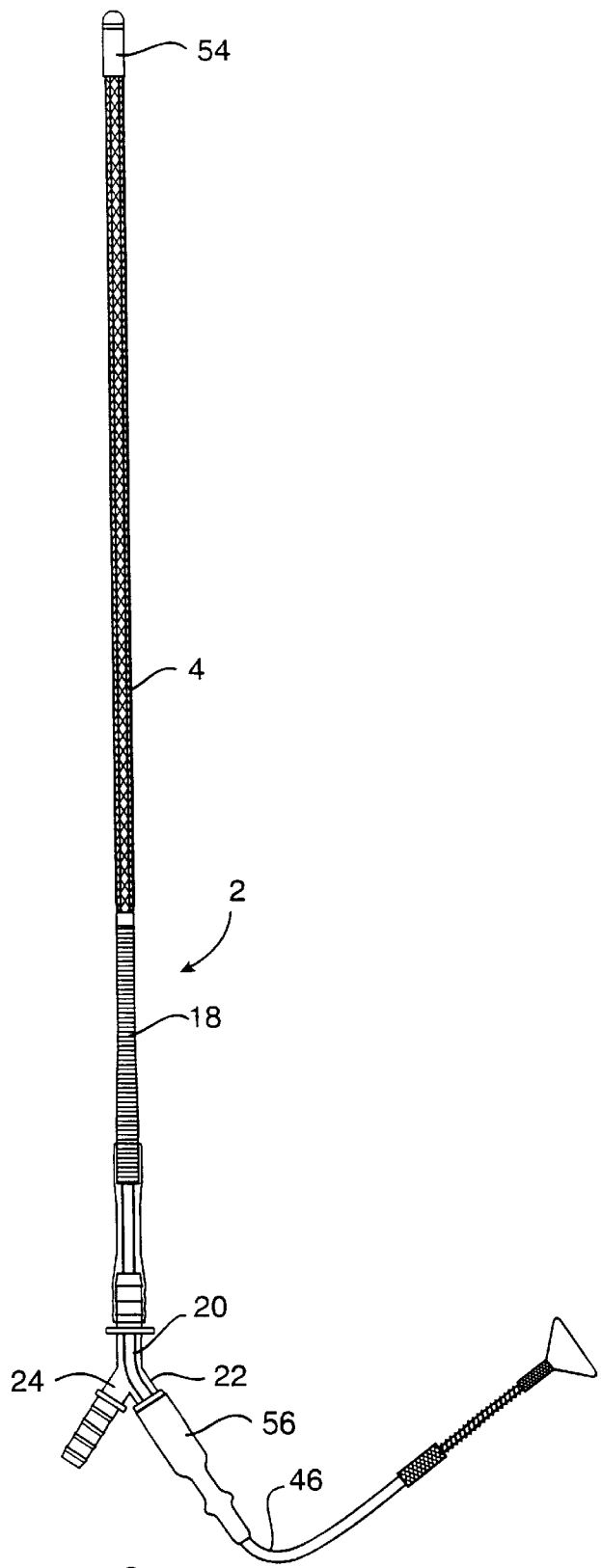
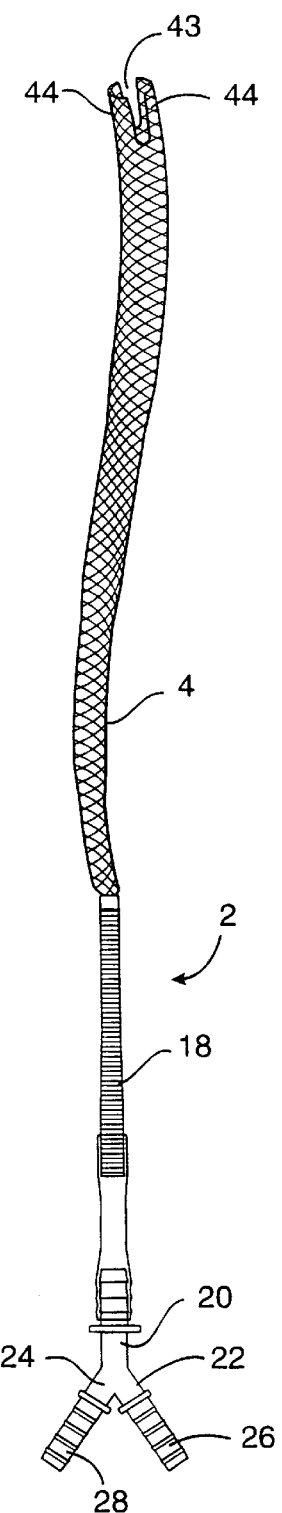
FIG. 1
FIG. 2

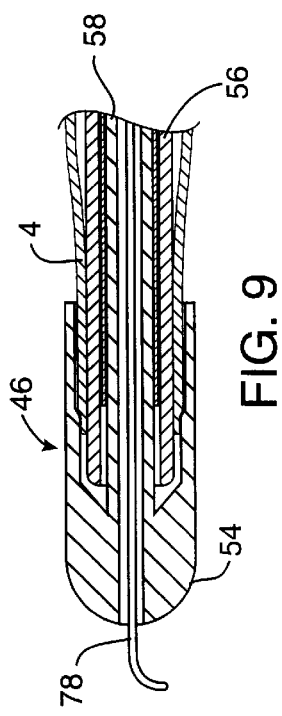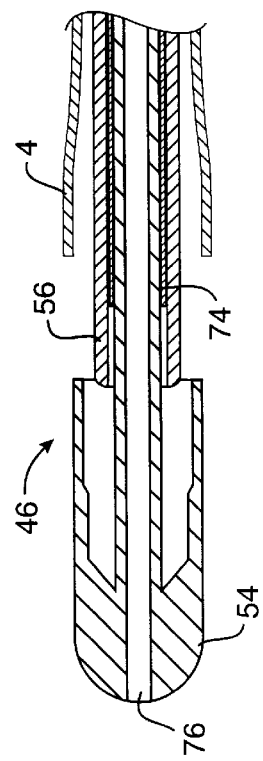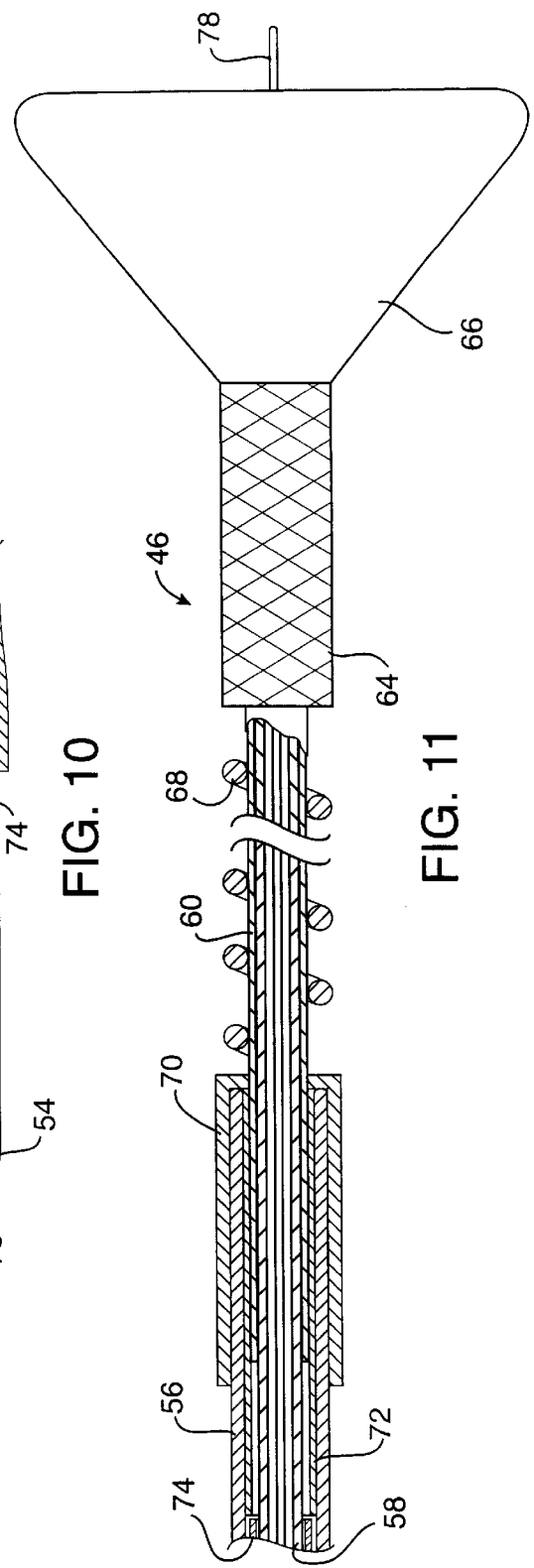

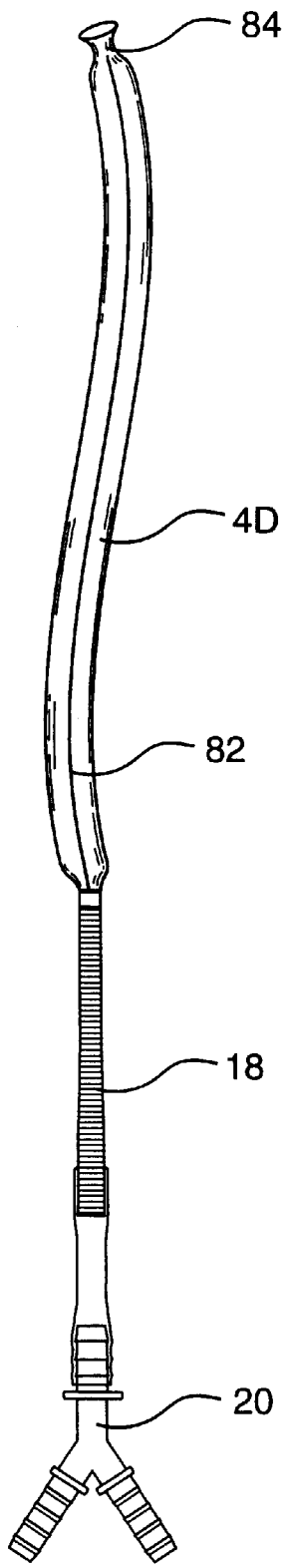
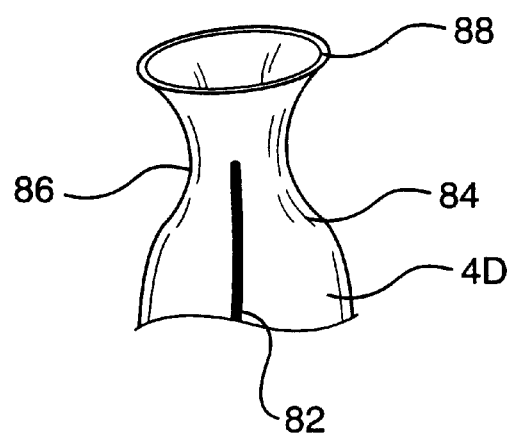
FIG. 15
FIG. 14

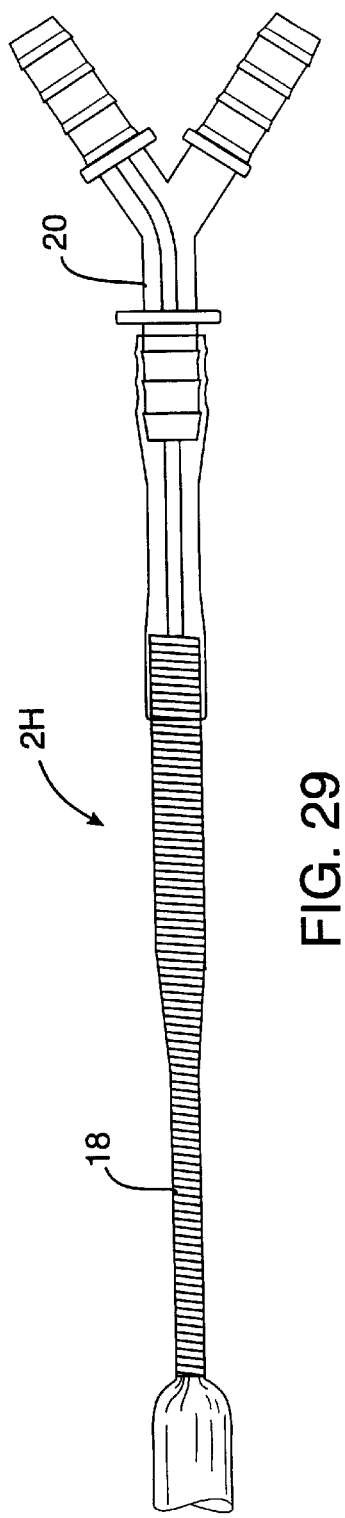
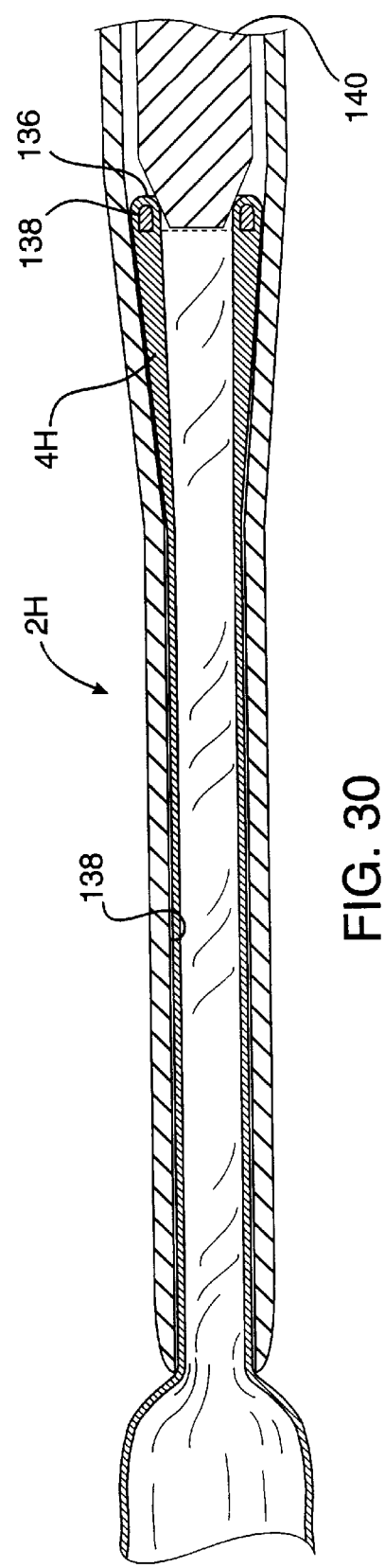
FIG. 29
FIG. 30

METHODS AND DEVICES FOR CANNULATING A PATIENT'S BLOOD VESSEL

BACKGROUND OF THE INVENTION

The present invention is related to introducer sheaths and cannulae for the introduction of catheters and the like into a patient's vascular system. Introducer sheaths are relatively rigid tubes which generally do not extend very far into the patient's vascular system since they are designed to merely provide access to the vascular system. A problem with conventional introducer sheaths is that they are generally not long enough to protect the vessel through which the catheter is advanced.

The present invention also relates to a cannula for introduction of catheters and infusion of fluids. Conventional Y-armed cannulae for introduction of catheters and infusion of fluids are relatively rigid tubes which also do not extend very far into the patient's vascular system. Thus, Y-armed cannulae are also generally not long enough to protect the vessel through which the catheter is advanced.

Thus, an object of the present invention is to provide an improved method and device for the introduction of catheters and the like.

Yet another object of the present invention is to provide an improved method and device for introduction of catheters and infusion of fluids.

Still another object of the present invention is to provide an improved method and device for cannulating a patient's blood vessel.

SUMMARY OF THE INVENTION

The present invention provides methods and devices for cannulating a blood vessel, introducing catheters and infusing fluids into the blood vessel. A cannula having an expandable portion is inserted into the blood vessel with the expandable portion in a collapsed position. After introduction into the blood vessel, the expandable portion is expanded to an expanded position. A medical procedure is then performed through the lumen of the expandable portion. In a preferred method, the surgical procedure includes passing a catheter through the expandable portion. The catheter may be any type of catheter and is preferably an aortic occlusion catheter having a balloon for occluding the ascending aorta and a lumen for delivering cardioplegic fluid. An advantage of the expandable portion is that the cannula can be passed through relatively small, tortuous vessels in the collapsed condition thereby minimizing trauma to the vessel. The expandable portion is then able to protect at least a portion of the vessel through which the catheter is advanced.

The surgical procedure performed through the expandable portion may also be simply infusion of a fluid such as oxygenated blood. In another aspect of the preferred method, the fluid is infused into the patient's vascular system in a retrograde direction so that the expandable portion protects the blood vessel from retrograde fluid forces. A specific application is retrograde delivery of oxygenated blood through the femoral artery.

The expandable portion is preferably permeable so that fluid passes through the wall of the expandable portion. The permeable expandable portion is particularly useful in perfusing side branches of the vessel in which the expandable portion is positioned. A sheath may be positioned on a radially inner and/or outer surface of the expandable portion to reduce fluid flow losses, provide a smooth inner surface for advancement of the catheter and/or reduce the permeability of the expandable portion.

A preferred material for the expandable portion is a fabric with the preferred fabric being a braided fabric. The fabric is preferably made of both yarn and monofilament fibers but may also be made of substantially only monofilament fibers or yarn. An introducer passes through the cannula and holds the cannula in the collapsed position for introduction into the patient. In a preferred embodiment, the introducer has a tip which holds the distal end of the expandable portion and applies a tensile force to the expandable portion to radially contract the expandable portion and maintain the expandable portion in the collapsed position.

These and other aspects of the invention will become apparent from the following description of the preferred embodiments.

BRIEF DESCRIPTION OF THE DRAWINGS

FIG. 1 shows a cannula having an expandable portion held in a collapsed position by an introducer;

FIG. 2 shows the expandable portion in an expanded position;

FIG. 9 is a cross-sectional view of a distal end of the introducer with a tip in a closed position;

FIG. 10 is a cross-sectional view of the distal end of the introducer with the tip in an open position;

FIG. 11 is a cross-sectional view of a proximal end of the introducer;

FIG. 14 shows another expandable portion in an expanded position;

FIG. 15 shows a distal end of the expandable portion of FIG. 14;

FIG. 29 shows another method of deploying the expandable portion;

FIG. 30 is a cross-sectional view of the cannula of FIG. 29;

DESCRIPTION OF THE PREFERRED EMBODIMENTS

Referring to FIG. 1 a cannula 2 in accordance with the present invention is shown. The cannula 2 includes an expandable portion 4 which is movable from the collapsed position of FIG. 1 to the expanded position of FIG. 2. The term cannula as used herein refers to any cannula, catheter, tube, introducer sheath, trocar or the like which is inserted into a patient's vascular system for delivery or withdrawal of fluids and/or introduction of catheters and the like.

Figure 3:
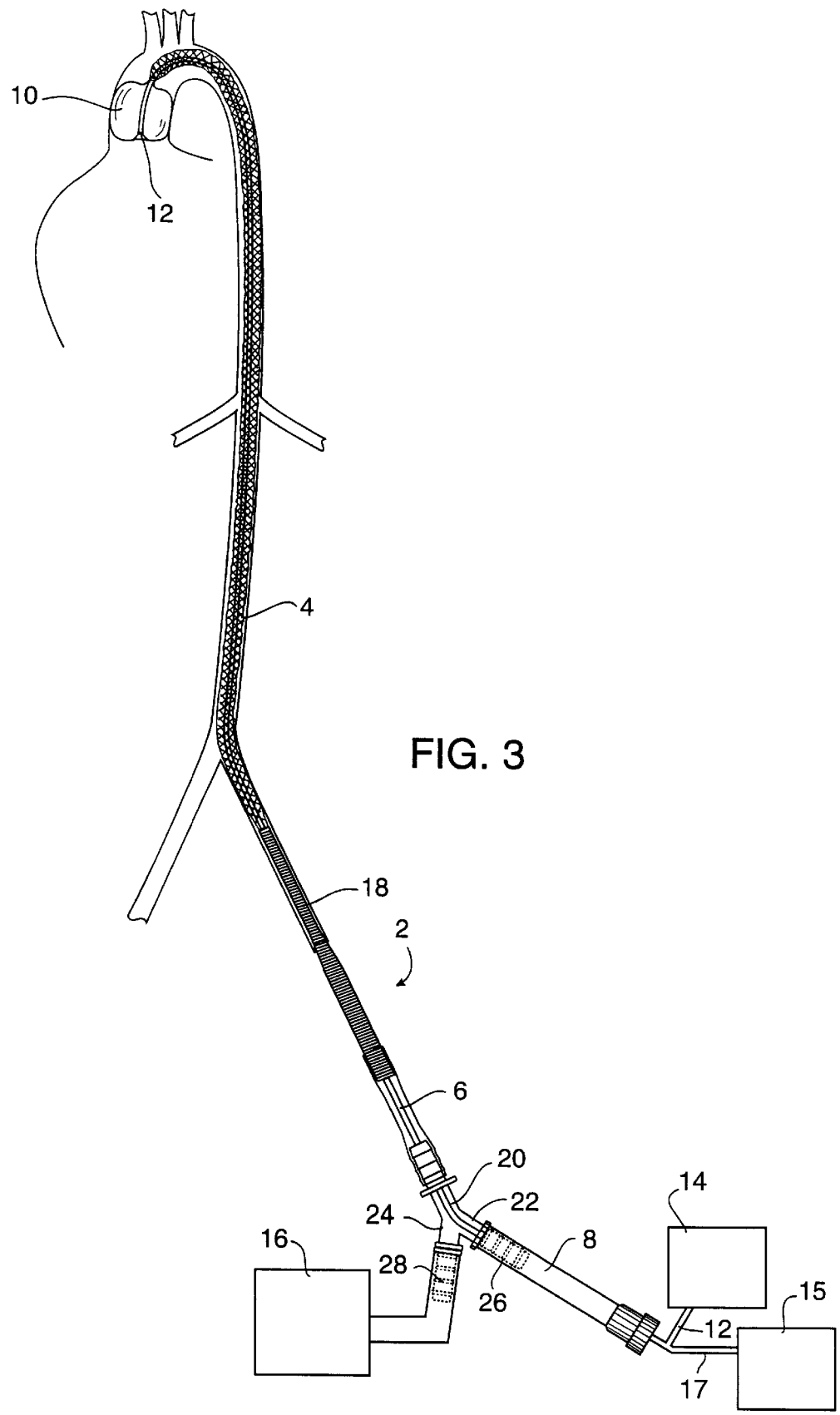
FIG. 3 shows the cannula of FIG. 1 inserted into the femoral artery with the expandable portion extending to the patient's aortic arch.
Figure 4:
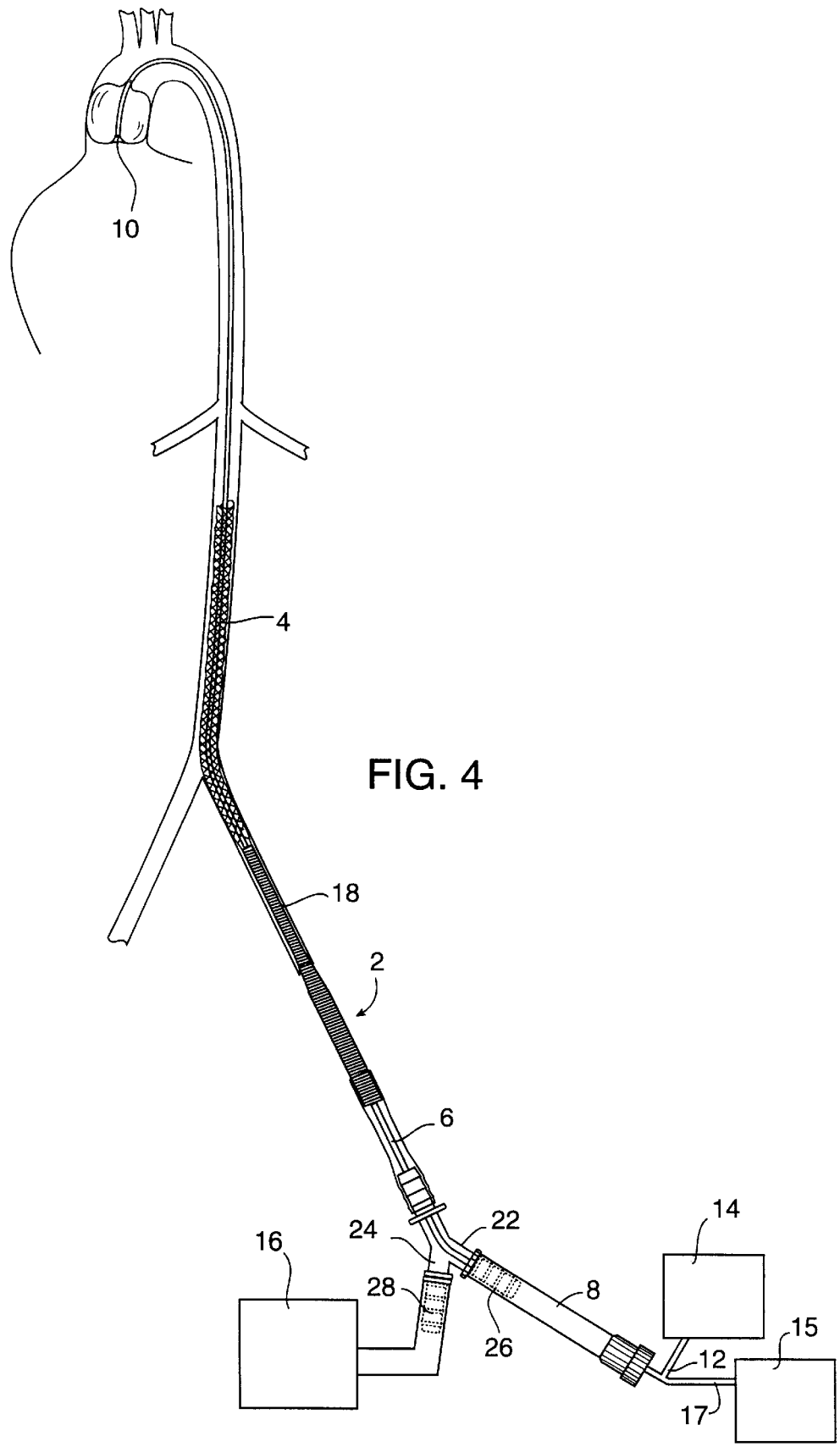
FIG. 4 shows the expandable portion extending beyond the bifurcation of the abdominal aorta and the distal to the renal arteries.

Referring to FIGS. 3 and 4, the cannula 2 is preferably configured to receive a catheter 6 for introducing the catheter 6 into the patient's vascular system. An advantage of the cannula 2 is that it can be advanced into relatively small, tortuous vessels in the collapsed position and then expanded to protect the vessel when advancing the catheter 6 through the vessel. The cannula 2 has a hemostasis valve 8, which is preferably a Tuohy-Borst valve, to provide a fluid tight seal between the cannula 2 and catheter 6 while permitting advancement of the catheter 6 relative to the cannula 2. In a specific application of the present invention, the catheter 6 has an occluding member 10, which is preferably a balloon, to occlude the patient's ascending aorta. The occluding member 10 is inflated through a lumen 17 with fluid from a source of inflation fluid 17. Such a catheter is disclosed in U.S. patent application Ser. No. 08/782,113 which is hereby incorporated by reference. The catheter 6 has a lumen 12 coupled to a source of cardioplegic fluid 14. Cardioplegic fluid is delivered to arrest the patient's heart and/or maintain the heart in an arrested state. Although use of the catheter 6 for occluding the patient's ascending aorta and delivering cardioplegic fluid is a preferred use of the catheter 6, any other catheter 6 may be used with the cannula 2 without departing from the scope of the invention. For example, the catheter 6 may be a PTCA catheter, stent delivery catheter, intra-aortic balloon pump, atherectomy catheter, TMR catheter, diagnostic catheter, biopsy catheter, or a general vascular occlusion catheter.

Referring to FIG. 3, the cannula 2 is also preferably used to infuse a fluid into the patient. A specific application of the cannula 2 is for returning oxygenated blood to the patient from a source of oxygenated blood 16 which is preferably a bypass system. The bypass system delivers oxygenated blood to the patient for complete bypass support when the patient's heart is arrested. The bypass system preferably includes a pump, filter, bubble trap, heat exchanger and an oxygenator, however, the patient's own lungs may also be used to oxygenate the blood. Although a specific application of the present invention is for delivery of oxygenated blood, the cannula 2 of the present invention may be used to deliver any other fluid to the patient's vascular system.

The expandable portion 4 is particularly useful when passing the catheter 6 and a fluid through the cannula 2 since the expandable portion 4 makes it possible to provide a longer cannula 2 to protect the vessel through which the catheter 6 is advanced while retaining adequate fluid flow characteristics. The expandable portion 4 also advantageously protects the vessel from retrograde fluid forces. When inserting the cannula 2 into a vessel such as the femoral artery and infusing fluid into the patient's vascular system through the cannula 2, the fluid moves in a retrograde direction, that is, in a direction opposite to normal blood flow. The expandable portion 4 advantageously protects the vessel from retrograde fluid forces.

Referring to FIGS. 2 and 3, the expandable portion 4 is attached to a wire-reinforced tube 18. The tube 18 is attached to a body 20 having first and second arms 22, 24. The first arm 22 has a barbed connector 26 which receives the hemostasis valve 8 and the second arm 24 has a barbed connector 28 which is coupled to the source of oxygenated blood 16. Any conventional tube 18 and body 20 may be used with the expandable portion 4 to form the cannula 2 of the present invention such as the tube 18 and body 20 disclosed in U.S. patent application Ser. No. 08/749,683 which is hereby incorporated by reference.

The expandable portion 4 preferably has a maximum outer dimension of no more than 0.30 inch, more preferably no more than 0.25 inch, and most preferably no more than 0.16 inch when in the collapsed condition. The expandable portion 4 preferably has a minimum inner dimension of at least 0.31 inch, more preferably at least 0.41 inch and most preferably at least 0.51 inch when in the expanded condition.

Referring to FIG. 4, the distal tip of the expandable portion 4 lies between the aortic bifurcation and the renal arteries when inserted into the femoral artery so that retrograde fluid forces are not exerted on the femoral, external iliac and common iliac arteries. Alternatively, the expandable portion 4 can be sized to extend all the way to the aortic arch as shown in FIG. 3 so that the descending, thoracic and abdominal aorta are not exposed to retrograde fluid forces. The expandable portion 4 preferably has a length of at least 2 cm, 4 cm, 10 cm, 25 cm, 40 cm or at least 70 cm depending upon the particular use.

Figure 6:
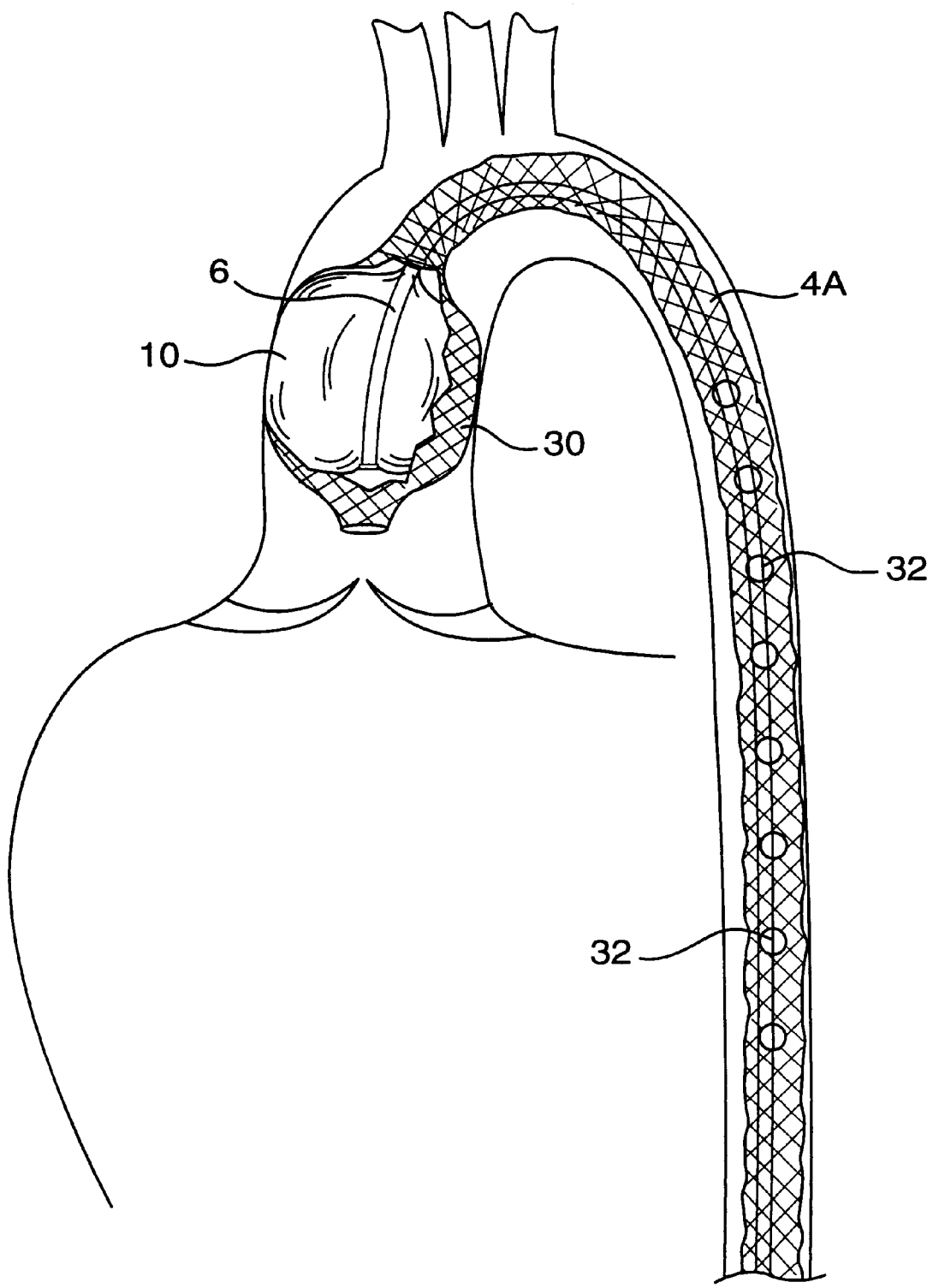
FIG. 6 shows the expandable portion extending around an occluding member of the catheter.

Referring to FIG. 6, a second, preferred expandable portion 4A is shown which has a distal portion 30 sized to extend around the occluding member 10 of the catheter 6 so that the expandable portion 4A can move into sealed contact with the blood vessel. In a preferred embodiment, the distal portion 30 of the expandable portion 4A expands to a diameter of at least 1.50 inch and more preferably at least 2.00 inch. The expandable portion 4A can help reduce migration of the occluding member 10 since the expandable portion 4A may provide better frictional resistance to migration than the occluding member 10. The expandable portion 4A also has side holes 32 which enhance fluid flow through the expandable portion 4A and delivers fluid to predetermined locations along the expandable portion 4A. The expandable portion 4A may be made of any of the materials described herein.

The expandable portion 4, 4A is preferably permeable so that fluid, such as oxygenated blood, may pass therethrough. An advantage of providing a permeable expandable portion 4, 4A is that side vessels, such as the renal arteries, may be fed with fluid which may not occur when using an impermeable cannula. The expandable portion 4, 4A preferably has a porosity of at least 100, more preferably 1000 and most preferably 3000 cubic centimeters of water per square centimeter of surface area per minute at 100 mm Hg.

Figure 5:
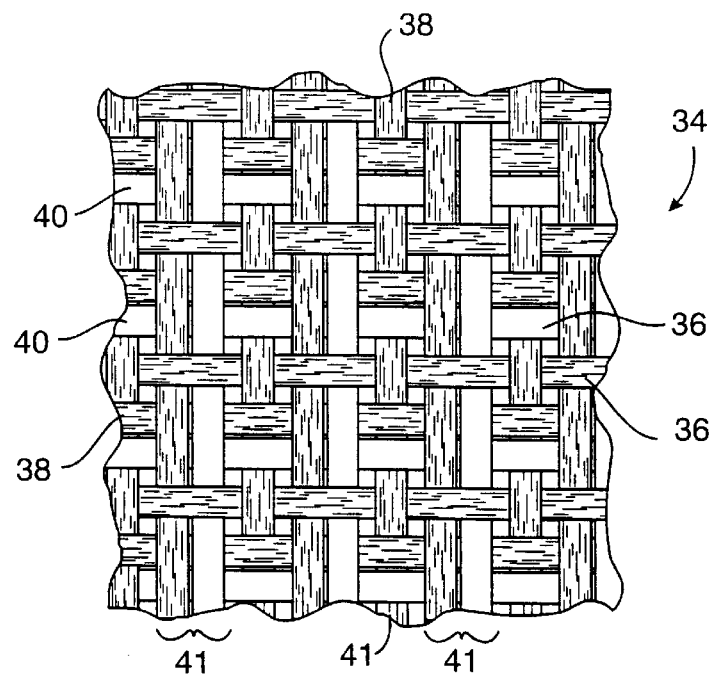
FIG. 5 shows a first, preferred fabric for the expandable portion.

Referring to FIG. 5, the expandable portion 4 may be made of any suitable material and a preferred material is a fabric 34. The term fabric as used herein refers to any structure produced by interlacing fibers 36. Such structures include bonded, braided, knitted and woven fabrics with a preferred fabric being braided. The fabric 34 is preferably formed as a tube, however, the fabric 34 may also be formed from a flat sheet with the sides joined together to form a tube. The term fiber as used herein refers to any threadlike material which is adaptable for spinning, weaving, felting and similar applications. The fibers 36 may be inorganic or organic. Furthermore, the fibers 36 may be yarn fibers 38, which are formed from a number of filaments, or monofilament fibers 40, which are made from a single filament. Preferred materials for the fibers 36 include polyester, polyethylene, nylon, polyolefin, polypropylene, PTFE and polyurethane.

The fabric 34 preferably has at least 16 ends 41, more preferably at least 32 ends 40 and most preferably at least 64 ends 41. The term "end" as used herein refers to one or more fibers 36 held by a carrier of a weaving or braiding machine forming the fabric 34. Thus, the number of ends 41 in the fabric 34 is the same as the number of carriers in the weaving or braiding machine forming the fabric 34. Each carrier may carry more than one fiber 36 so that the number of fibers 36 is not necessarily the same as the number of ends 41. A preferred number of fibers 36 in the fabric 34 is preferably at least 64, more preferably at least 80 and most preferably at least 96.

Referring to FIG. 5, the fabric 34 is preferably cobraided with the yarn fibers 38 and the monofilament fibers 40. The yarn fibers 38 are preferably polyester having a denier of between 150 and 1200, more preferably between 150 and 600 and most preferably about 250. The monofilament fibers 40 provide column strength so that the catheter 6 can be withdrawn if necessary. The monofilament fibers 40 also provides resiliency which tends to bias the expandable portion 4 toward the expanded position when in the collapsed position. The monofilament fibers 40 are preferably made of polyester with a diameter between 0.002 and 0.016 inch, more preferably between 0.003 and 0.012 inch, and most preferably between 0.004 and 0.008 inch. The monofilament fibers 40 preferably have a Rockwell hardness of at least R105 and more preferably at least R110 and most preferably about R115.

The fabric 34 preferably has 64 ends 41 which means that the weaving machine forming the fabric has 64 carriers. Each carrier will carry either one yarn fiber 38 alone or both one yarn fiber 38 and one monofilament fiber 40. Preferred ratios of yarn fibers 38 to monofilament fibers 40 are at least 1 to 1, at least 2 to 1, and at least 3 to 1. A preferred number of monofilament fibers 40 is 32. Thus, 32 carriers of the 64 carrier weaving machine carry both yarn fibers 38 and monofilament fibers 40 while 32 carriers carry only yarn fibers 38. The fabric 34 is preferably a diamond braid having a braid angle of between 60° and 120° and more preferably about 90°. The fabric 34 is preferably balanced so that the fabric 34 does not twist when moving from the collapsed position to the expanded position. The monofilament fibers 40 are equally distributed between right and left hand winding.

After forming the expandable portion 4, the expandable portion 4 is mounted on a tapered mandrel (not shown) and then heated to about 350° F. to set the expandable portion in the natural, unbiased or "neutral" position of FIG. 2. The expandable portion 4 initially has an inner diameter of about 0.27 inch for a length of about 1 inch. The expandable portion 4 then flares outwardly at about 5.5 (degrees) to an inner diameter of about 0.32 inch which remains constant for about 1.86 inches. The expandable portion then expands at about 6.0 (degrees) to an inner diameter of 0.37 inch which remains constant for 1.67 inches. The expandable portion 4 then expands again at 6.0 degrees to a final inner diameter of 0.45 inch which remains constant for about 2.67 inches. The neutral position described above is used with a 23 French tube 18, however, the neutral position may be altered depending upon the size of the tube 18 and the particular application of the present invention.

Referring to FIG. 2, a distal end 42 is cut to produce two extensions 44 with a slot 43 therebetween. The extensions 44 and slot 43 reduce the amount of fabric at the distal end 42 so that the distal end 42 more easily fits into an introducer 46 (FIG. 1) which is described in greater detail below. The distal end 42 is cut ultrasonically or with a hot knife or laser to form the two extensions 44 and fuse together the distal end of the fibers 38, 40. The expandable portion 4 is then preferably coated with a radiopaque material such as platinum or gold. The radiopaque material may be deposited in any manner and is preferably deposited by ion beam assisted deposition (IBAD) or unbalanced magnetron sputtering. The expandable portion 4 is then preferably coated with heparin and the proximal end is dipped in urethane and bonded to the end of the tube 18. A conventional lubricious coating may also be applied to the expandable portion 4.

Figure 8:
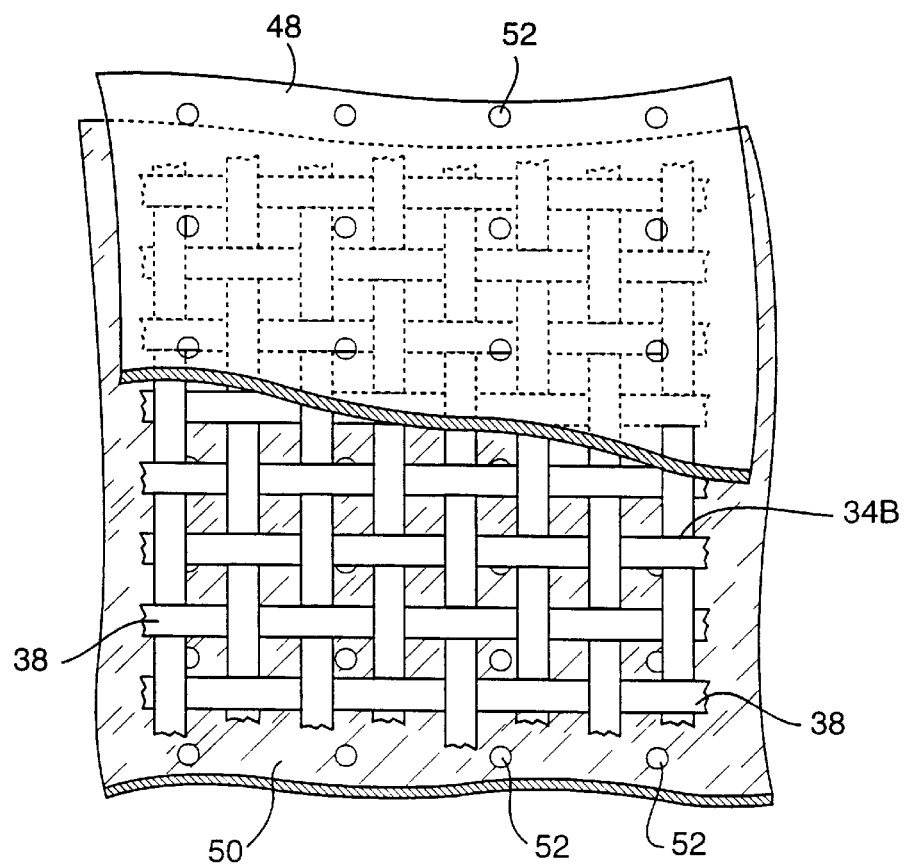
FIG. 8 shows a second, preferred fabric for the expandable portion.
Figure 7:
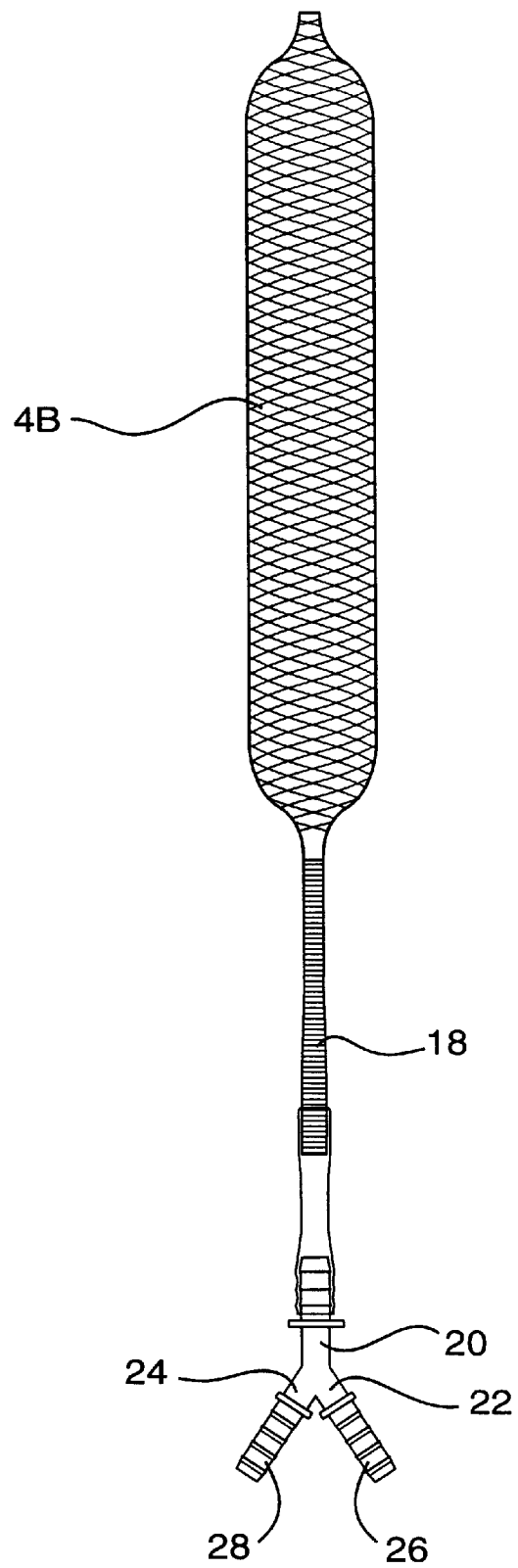
FIG. 7 shows a second, preferred cannula in an expanded position.

Referring to FIG. 7, another preferred expandable portion 4B is shown in the expanded position. The expandable portion 4B has the same shape as the expandable portion 4 above when in the collapsed position of FIG. 1. Referring to FIG. 8, the expandable portion 4B is made of another fabric 34B made of substantially only the monofilament fibers 40. The monofilament fibers 40 may be made of polyester, polyethylene, nylon, polyolefin, polypropylene or polyurethane and is preferably made of polyester. The monofilament fibers 40 preferably have a diameter of between 0.004 and 0.008 inch. The monofilament fibers are braided with a 48 carrier weaving machine with the resulting expandable portion 4b having a diameter of at least 0.300 inch and more preferably at least 0.500 inch in the expanded position. The weaving machine is preferably configured to provide a diamond braid having a braid angle of between 60° and 120° and more preferably about 90°

A first sheath 48 is positioned over the fibers 38B to provide a smooth outer surface and to reduce the permeability of the relatively open structure of the fabric 38B. A second sheath 50 may also be positioned on the inner surface to reduce pressure losses and provide a smooth surface for advancing the catheter 6 through the cannula 2. The first and second sheaths 48, 50 have holes 52 therein to provide the preferred permeability and porosity described above. The first and second sheaths 48, 50 are preferably attached to the expandable portion 4B only at proximal and distal ends so that the fibers 38B are free to displace relative to the first and second sheaths 48, 50 between the proximal and distal ends.

The first and second sheaths 48, 50 may be inelastic or elastic. When using an elastic first sheath 48, the first sheath 48 preferably biases the expandable portion 4B toward the expanded position so that when the introducer 46 releases the expandable portion 4B, the expandable portion 4B moves to the expanded position of FIG. 7. The first sheath 48 is attached to the expandable portion 4B by stretching the first sheath 48 and attaching the ends of the first sheath 48 to the ends of the fabric 34B. Thus, the first sheath 48 applies a compressive force to the fabric 34B when released thereby moving the fabric 34B to the expanded position. When using an elastic first sheath 48, the first sheath 48 is preferably made of styrene ethylene butylene styrene having a thickness of about 0.005 to 0.010 inch. Alternatively, the first and second sheath 48, 50 may be made of polyurethane having a wall thickness of about 0.003 to 0.008 inch when using inelastic first and second sheaths 48, 50.

Referring again to FIG. 1, the introducer 46 holds the expandable portion 4 in the collapsed position when introducing the cannula 2 into the patient's blood vessel. After the cannula 2 is inserted into the patient's blood vessel, the introducer 46 releases the expandable portion 4 thereby permitting the expandable portion 4 to assume the expanded position. The introducer 46 has a tip 54 which holds the distal end of the expandable portion 4 and exerts a tensile force on the expandable portion 4 so that the expandable portion 4 radially contracts to the collapsed position. An advantage of the preferred expandable portions 4 described above is that the expandable portions 4 radially contract to the collapsed position upon application of a tensile force. Another hemostasis valve 56 provides a fluid tight seal between the introducer 46 and the cannula 2.

The tip 54 of the introducer 46 is movable from the closed position of FIG. 9 to the open position of FIG. 10. When the tip 54 is in the closed position, the distal end of the expandable portion 4 is trapped between an outer tube 56 and the tip 54. When the tip 54 is moved to the open position, the expandable portion 4 is released. The expandable portion 4 is preferably configured to move proximally away from the tip 54 when released as shown in FIG. 10. After releasing the distal end of the expandable portion 4, the introducer 46 is then withdrawn from the cannula 2.

Referring to FIGS. 9–11, the tip 54 is attached to a flexible inner tube 58. The inner tube 58 is coupled to a rod 60 which in turn is coupled to a spring cap 64. An actuator 66 is attached to the spring cap 64 so that movement of the actuator 66 moves the tip 54 between the open and closed positions. A spring 68 biases the tip 54 toward the closed position. The spring 68 engages a tube collar 70 on one side and the spring cap 64 on the other. The tube collar 70 also receives a rigid support tube 72 which helps guide movement of the rod 60. A teflon liner 74 provides a low friction interface between the inner and outer tubes 58, 56. A throughhole 76 extends through the actuator 66, tube 58, rod 60 and tip 54 for receipt of a guidewire 78 which is advanced ahead of the introducer 46. Although it is preferred to use the introducer 46, the expandable portion 4 may also be folded into the collapsed shape, inserted into a hollow tube, or everted from the cannula 2 body without departing from the scope of the invention. Furthermore, use of the introducer 46 in connection the expandable portion 4 as described above is equally applicable to use of the introducer 46 for the expandable portions 4A, 4B.

Figure 12:
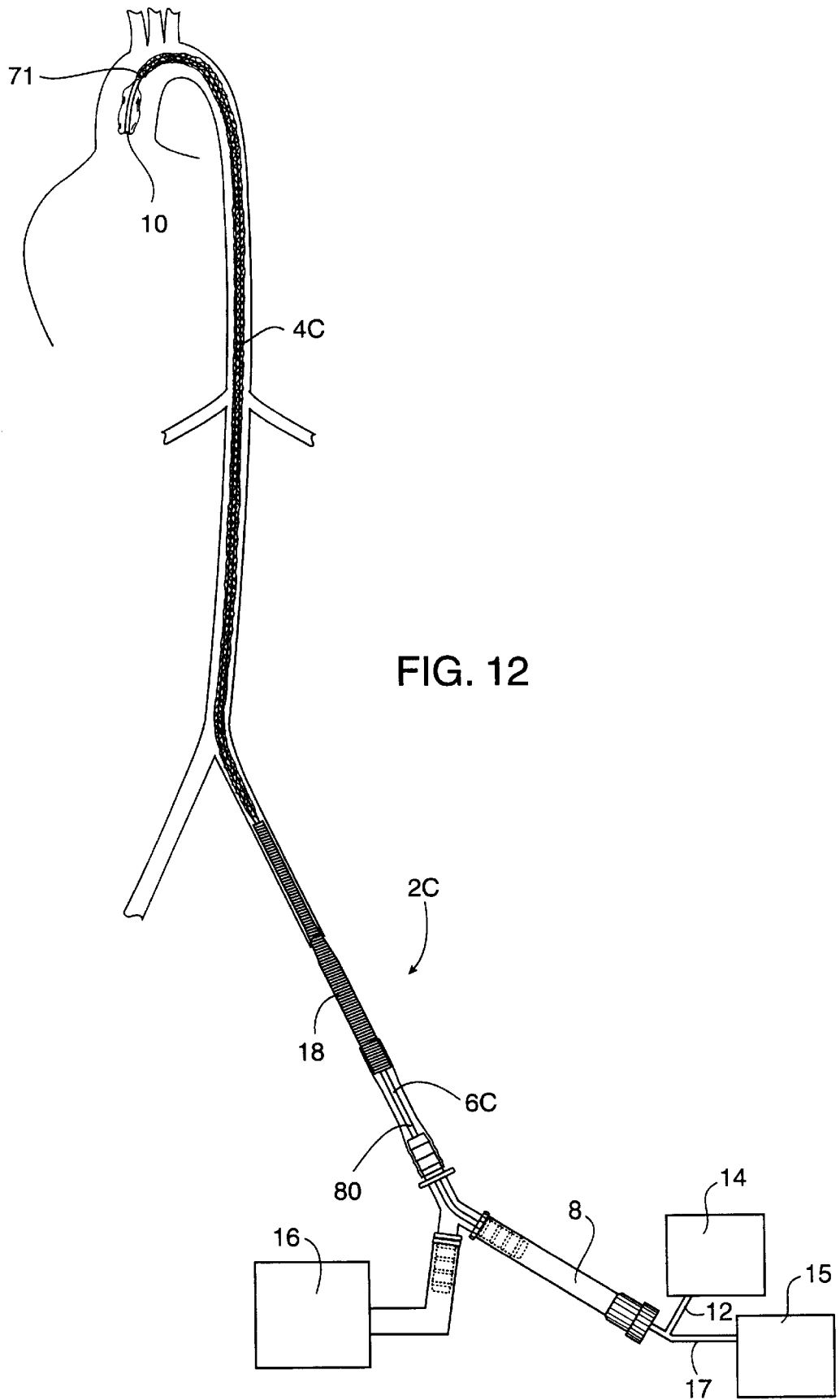
FIG. 12 shows a third preferred cannula with the occluding member in a collapsed position.
Figure 13:
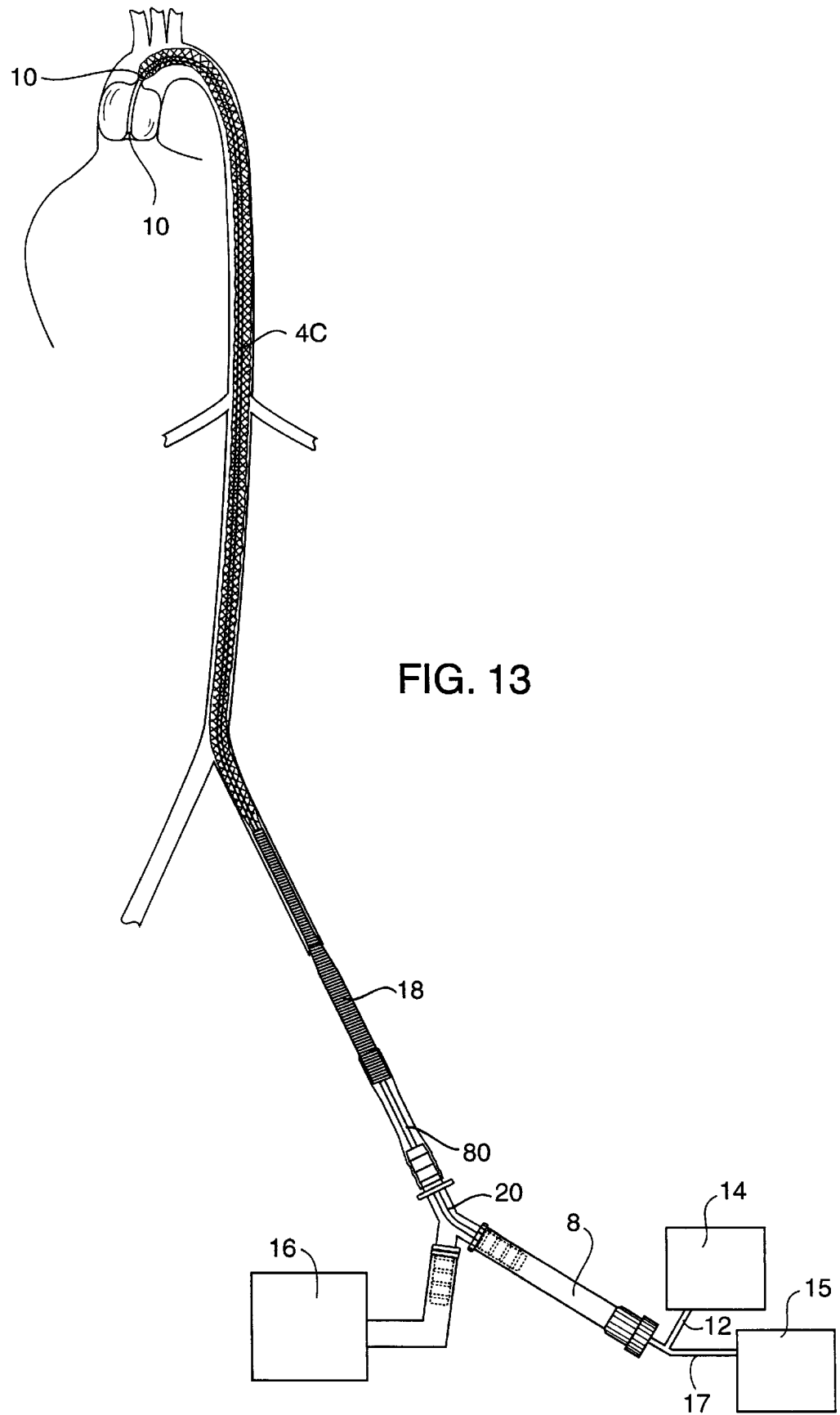
FIG. 13 shows a fourth preferred cannula with the occluding member in an expanded position.

Referring to FIGS. 12 and 13, another preferred cannula 2C is shown with a distal end 71 of an expandable portion 4C attached to the catheter 6C so that introduction of the catheter 6C and cannula 2C is accomplished in a single step. Like reference number refers to like or the same structure as the embodiments described above. The distal end 71 of the expandable portion 4C is bonded to a shaft 80 of the catheter 6C by capturing the expandable portion 4C between layers of melted polyurethane. The expandable portion 4C is not attached to the rest of the catheter 6C along the length of the catheter 6C so that the expandable portion 4C is free to expand and displace relative to the shaft 80. The expandable portion 4C and catheter 6C are preferably the same as described above in connection with FIGS. 2–5. An advantage of adding the expandable member 4C to the catheter 6C is that the catheter 6C can be introduced into the patient in the collapsed position so that the catheter 6C can be advanced through smaller, tortuous vessels. The femoral artery, for example, can be somewhat small and tortuous and passing a rigid catheter such as the catheter described in U.S. Pat. No. 5,312,344 to Grinfeld can be challenging. The expandable portion 4C is preferably the same as the expandable portion 4 while the catheter 6C is preferably the same as the catheter 6 and the discussion above concerning the preferred dimensions and features of the expandable portion 4 and catheter 6 are equally applicable here.

The catheter 6C is introduced into the patient in the collapsed position until the occluding member 10 is positioned in the ascending aorta as shown in FIG. 12. The catheter 6C is then retracted relative to the cannula 2C so that the expandable portion 4C can move to the expanded position. The expandable portion 4C is then expanded and oxygenated blood is passed through the expandable portion 4C from the source of oxygenated blood 16 as shown in FIG. 13. The occluding member 10 is then inflated to occlude the patient's ascending aorta and cardioplegic fluid is delivered through the lumen to arrest the patient's heart and/or maintain the heart in an arrested state.

Referring to FIGS. 14 and 15, another expandable portion 4D is shown wherein like reference numbers refer to like structure. The expandable portion 4D is coupled to the tube 18 and body 20 as described above. The expandable portion 4D is preferably made of polyurethane having a wall thickness of about 0.002 inch. A longitudinal wire 82 is attached to the expandable portion 4D by at the proximal and distal ends by thermal welding between two sheets of polyurethane The wire 82 prevents the expandable portion 4D from buckling or collapsing when withdrawing the catheter 6 through the expandable portion 4D. A distal end 84 of the expandable portion 4D has a constriction 86 so that a backpressure is developed in the expandable portion 4D when flowing a fluid through the expandable portion 4D. The backpressure helps the expandable portion 4D maintain the expanded position after its has been placed in tortuous vessels so that the expandable portion 4D does not collapse or kink. Although it is preferred to use the constriction 86, any other feature may be used to create the backpressure including fins, a baffle or a number of small outlets. The distal end 84 also has a flared end 88 which expands after the constriction 86 to minimize pressure losses at the fluid exit. The expandable portion 4D is preferably 27 French before the constriction 86 and necks-down to 24 French at the constriction 86 then increases in size to 27 French again at the flared end 88. The expandable portion 4D is preferably folded into the collapsed position for introduction into the patient in the manner described below in connection with FIGS. 17–21.

Figure 16:
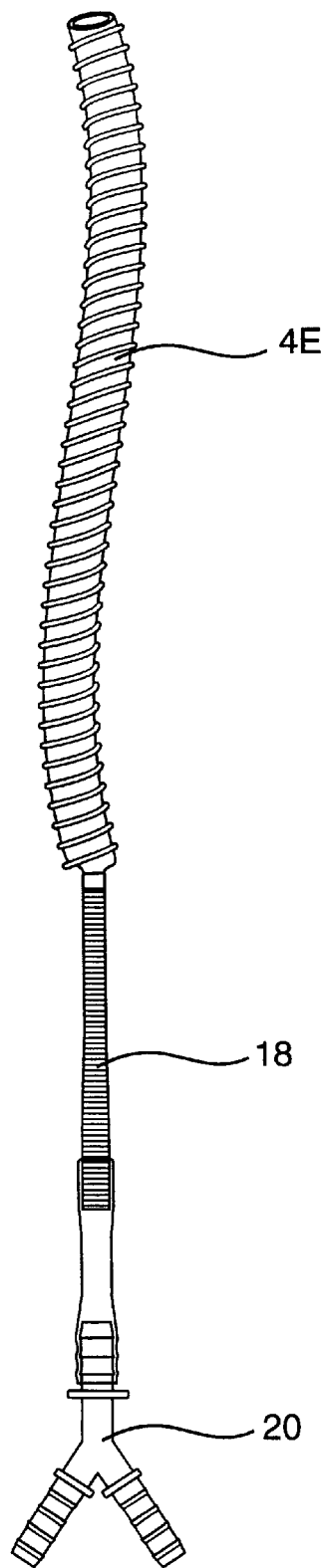
FIG. 16 shows yet another expandable portion in the expanded position.

Referring to FIG. 16, another expandable portion 4E is shown in the expanded position. The expandable portion 4E has a bellows construction which provides enhanced hoop strength to prevent kinking of the expandable portion 4E. The bellows construction may be constructed in any suitable manner. A preferred method of constructing the expandable portion 4E is to thermoform the bellow inside a coiled spring. The coils are formed by releasing the spring and capturing the thermally deformed material between the collapsed coils. Subsequent cooling sets the bellows. The expandable portion 4E is preferably introduced in the manner described below in connection with FIGS. 17–21.

Figure 17:
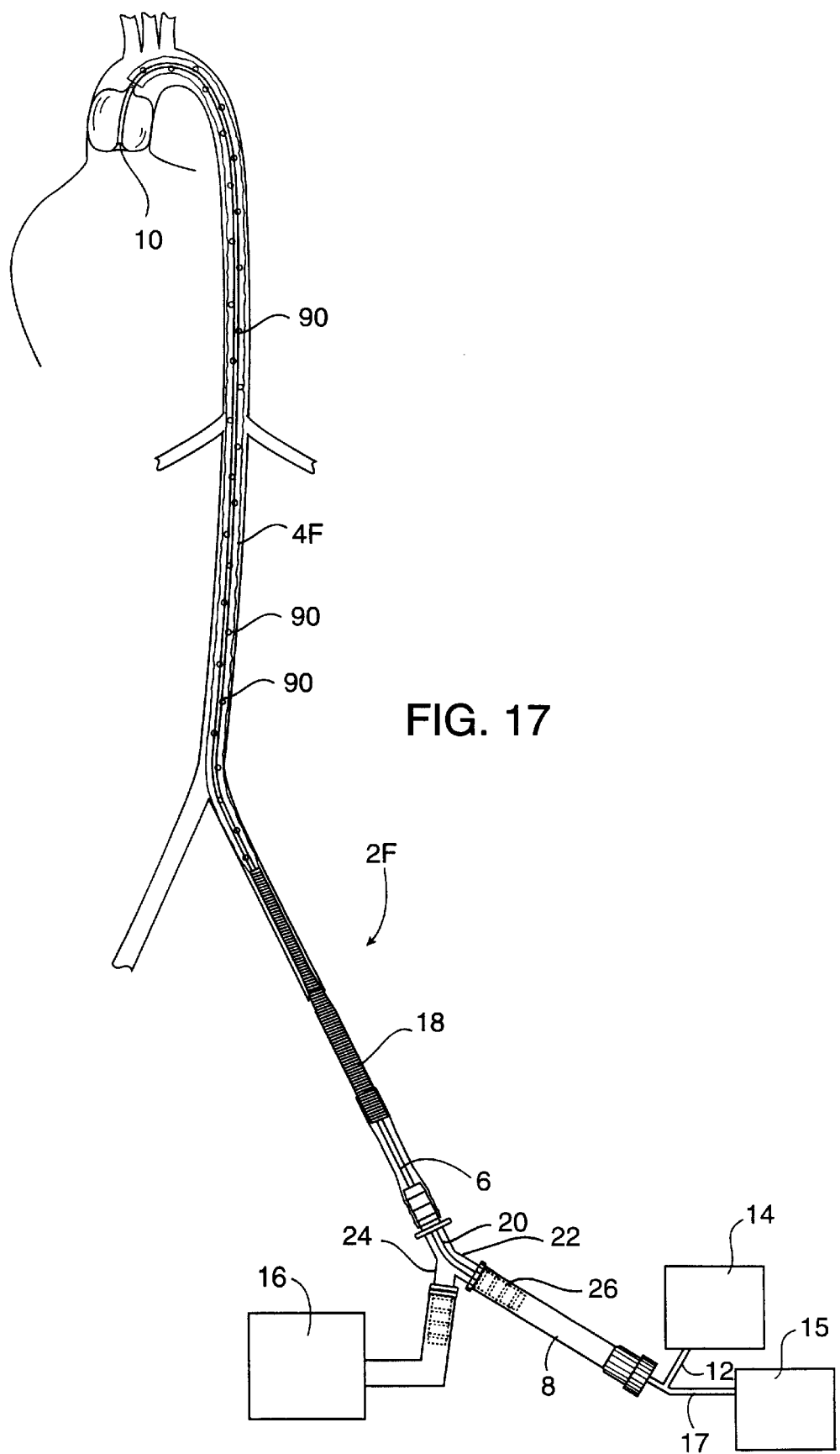
FIG. 17 shows still another expandable portion with the catheter passing therethrough.
Figure 18:
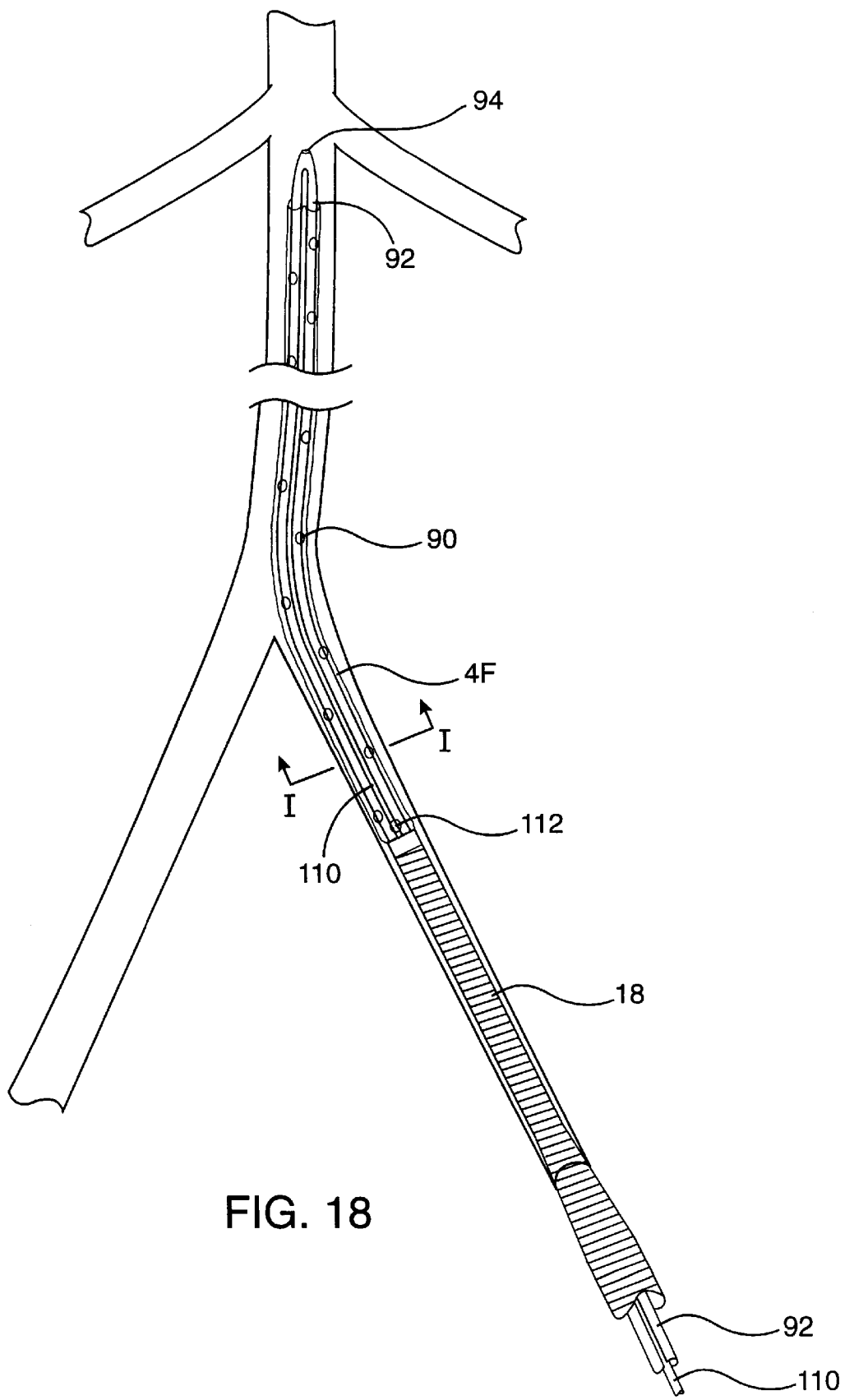
FIG. 18 shows the expandable portion of FIG. 17 inserted into a blood vessel with an introducer holding the expandable portion in a collapsed position.
Figure 19:
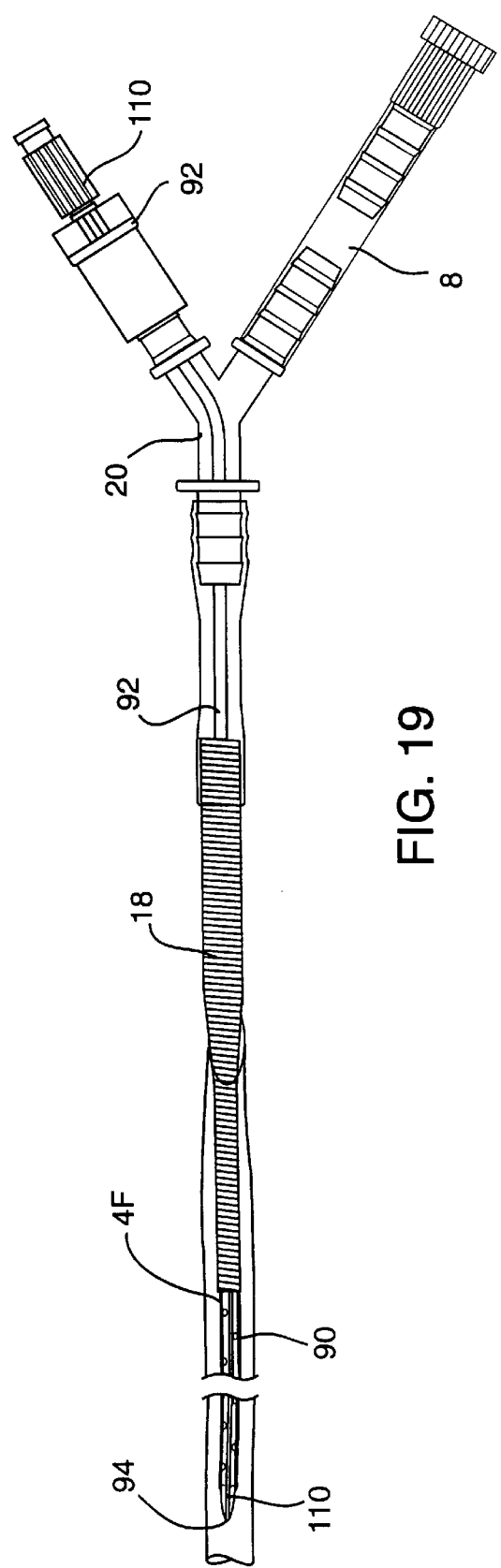
FIG. 19 shows the cannula of FIG. 18 inserted into a blood vessel.

Referring to FIGS. 17–19, yet another cannula 2F is shown where like reference numbers refers to like structure. The cannula 2F preferably has the tube 18 and body 20 described above in connection with FIGS. 1 and 2, however, any other structure may also be used. An expandable portion 4E is movable from the collapsed position of FIGS. 18 and 19 to the expanded position of FIG. 17. The catheter 6 described above extends through the cannula 2F and the discussion above concerning the use and construction of the catheter 6 is equally applicable here.

The cross-sectional area of the expandable portion 4F in the collapsed position is preferably between about 0.030 to 0.121 in$^2$ and more preferably about 0.035 to 0.065 in$^2$. In contrast, the cross-sectional area in the expanded position is preferably between about 0.071 to 0.196 in$^2$, more preferably about 0.071 to 0.121 in$^2$, and most preferably about 0.071 to 0.084 in$^2$. Alternatively, the expandable portion 4F may have the dimensions described above in connection with FIGS. 1–16. The expandable portion 4F is preferably made of polyurethane, polyethylene, styrene ethylene butylene styrene, polyolefin, polyester, polyvinyl chloride, PTFE, rubber (e.g., silicone, etc.) or any other suitable material.

The expandable portion 4F is substantially more flexible than the tube 18 and has a modulus of flexure of about 8,000 to 15,000 psi and more preferably about 10,000 to 12,000 psi. The wall thickness is preferably about 0.001 to 0.010 inch, more preferably about 0.001 to 0.005 inch, and most preferably about 0.001 to 0.002 inch. The minimum length of the expandable portion 4F is preferably at least about 3 times the length of the tube 18 or at least about 7, 12, 15 or 22 inches. Alternatively, the length of the expandable portion 4F can be the same as described above in connection with FIGS. 1–16.

The expandable portion 4F may include a plurality of openings 90 for discharge of fluid, such as oxygenated blood, along the length of the expandable portion 4F. The openings 90 may be distributed along the expandable member 4F to discharge fluid at predetermined locations and rates. The expandable portion 4F preferably has the permeability and porosity ranges described above in connection with FIGS. 1–7. The expandable portion 4F may also be terminated proximal to the occluding member.

Referring to FIGS. 18–21, an introducer 92 is configured for sliding receipt in the cannula 2F. As will be described below, the introducer 92 maintains the expandable portion 4F in the collapsed position for introduction into the patient's blood vessel. The introducer 92 has an atraumatic tip 94 extending beyond the expandable portion 4F to prevent injury to the vessel when advancing the cannula 2 through the vessel. The introducer 94 also has a proximal hub 96 with a luer lock connector 98 at the opposite end. The introducer 94 passes through a wiper-type hemostatic seal 100 in a connector plug 102 to form a fluid seal between the introducer 94 and cannula 2F. It should be understood that a variety of hemostasis valves may be used with the present invention, such as iris valves, without departing from the scope of the invention. The introducer 94 is preferably made of extruded polyurethane, however, any other suitable material may be used.

Figure 20:
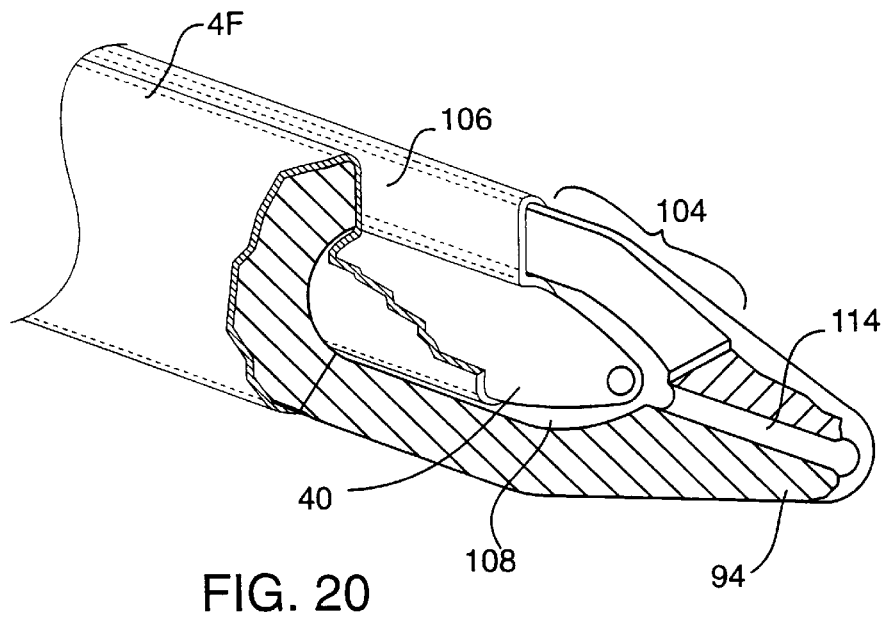
FIG. 20 is a fragmentary, enlarged front perspective view, partially broken away, of the expandable portion retained in a channel of the introducer.
Figure 21:
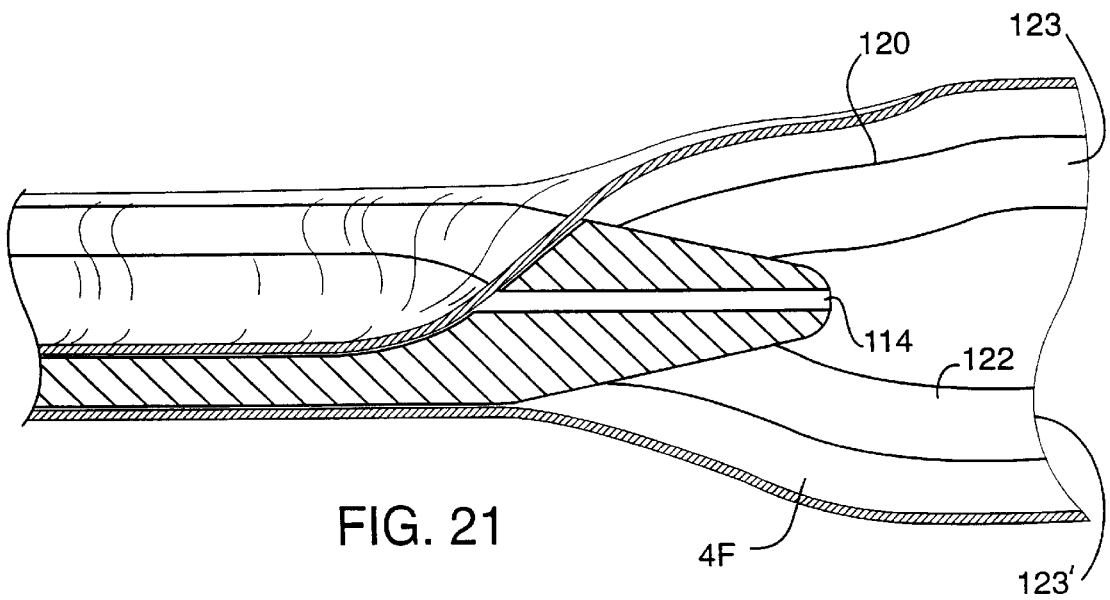
FIG. 21 is a fragmentary front perspective view, partially broken away, illustrating deployment of the expandable portion.
Figure 22:
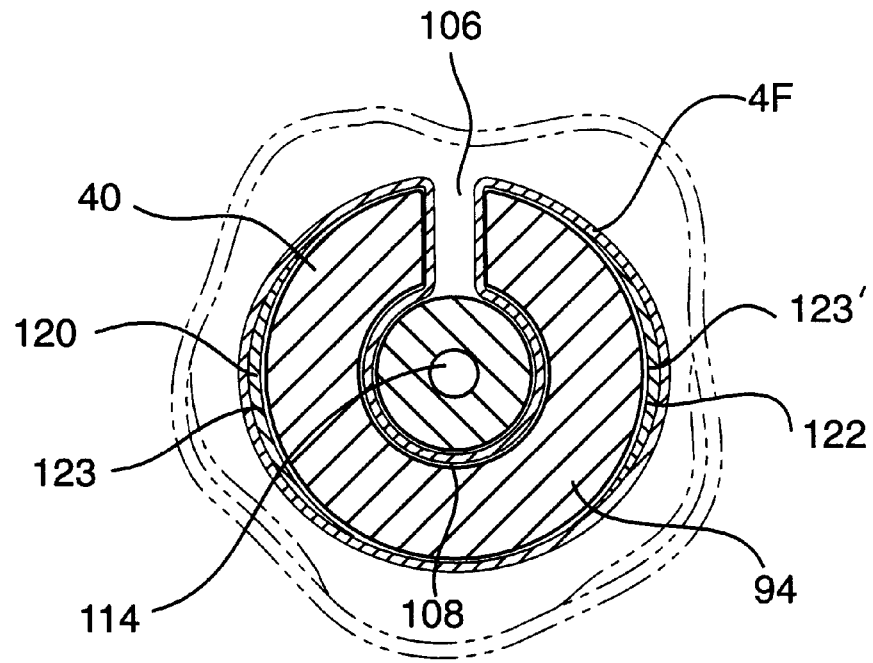
FIG. 22 is a cross-sectional view of the introducer and expandable portion of FIG. 18 along line I—I.
Figure 23:
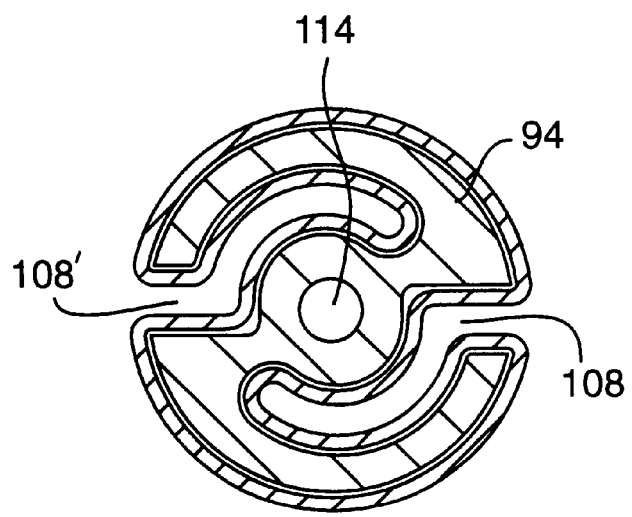
FIG. 23 is a cross-sectional view of an alternative embodiment of the introducer.

The introducer 94 includes a retaining structure 104 configured to retain the expandable portion 4F in the collapsed position. The retaining structure 104 has a slot 106 leading to a channel 108 which receives the expandable portion 4F. A retainer 110 passes through a hole 112 in the expandable portion 4F and is slidably disposed within the channel 108 to hold the expandable portion 4F in the channel 108. Channel 108 is preferably about 0.08 to 0.16 inch in diameter and terminates proximate to the tip 94. Referring to FIG. 22, a cross-sectional view of FIG. 18 along line I—I shows the retainer 110 holding the expandable portion 4F in the channel 108 of the introducer 94. Referring to FIGS. 20 and 21, a guidewire lumen 114 passes through the retainer 110 and introducer 94 and receives a guidewire which is preferably a 0.038 inch diameter guidewire. It will further be appreciated that two opposed channels 108, 108', as shown in FIG. 23, could be provided for receipt of the expandable portion 4F. In this configuration, the same diameter introducer 94 enables an even larger expanded position. While the channels 108 are preferably cylindrical, the channels 108 may take any other shape such as C-shaped.

Referring to FIGS. 20–22, the expandable portion 4F may include reinforcing 123 to prevent bunching of the expandable portion 4F when withdrawing the catheter 6 through the expandable portion 4F. Referring to FIGS. 5, 6 and 10, the reinforcing 123 extends longitudinally along the expandable portion 4F. The reinforcing 123 is preferably formed as two ribs 120, 122 each having an arc length of from about 5 to 180 degrees. The reinforcing 123 is preferably made of a biocompatible material such as urethane. The introducer 94, retainer 110 and tube 18 are preferably coated with a lubricious biocompatible coating such as polyvinyl pyrrolidone, however, any other suitable coating may be used.

In operation, the cannula 2F is inserted into the patient with the introducer 94 holding the expandable portion 4F in the collapsed position of FIGS. 18 and 19. The retainer 110 passes through the hole 112 and into channel 108 to hold the expandable portion 4F in the channel 108. The cannula 2F is introduced into the patient either percutaneously or by surgical cutdown with surgical cutdown being a preferred method. A suture 124 is tied around the artery at the cutdown to prevent bleeding from the vessel when inserting the cannula 2F. The guidewire is advanced ahead of the cannula 2F and the cannula 2F is then advanced over the guidewire to the desired location. The guidewire is removed and the retainer 110 and introducer 94 are withdrawn thereby permitting the expandable portion 4F to take the expanded position. The cannula 2F is then ready for any of the surgical procedures described above including insertion of the catheter 6 and/or infusion of fluid, such as oxygenated blood, as described above in connection with FIGS. 1–16.

Figure 24:
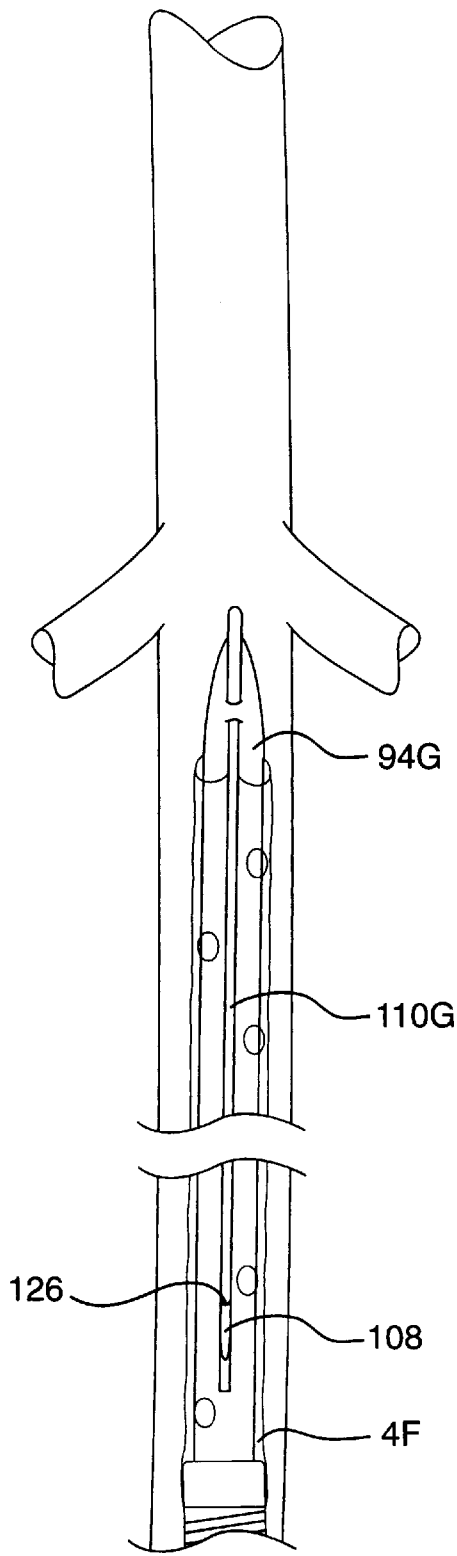
FIG. 24 shows another introducer with a retainer attached to the introducer.
Figure 26:
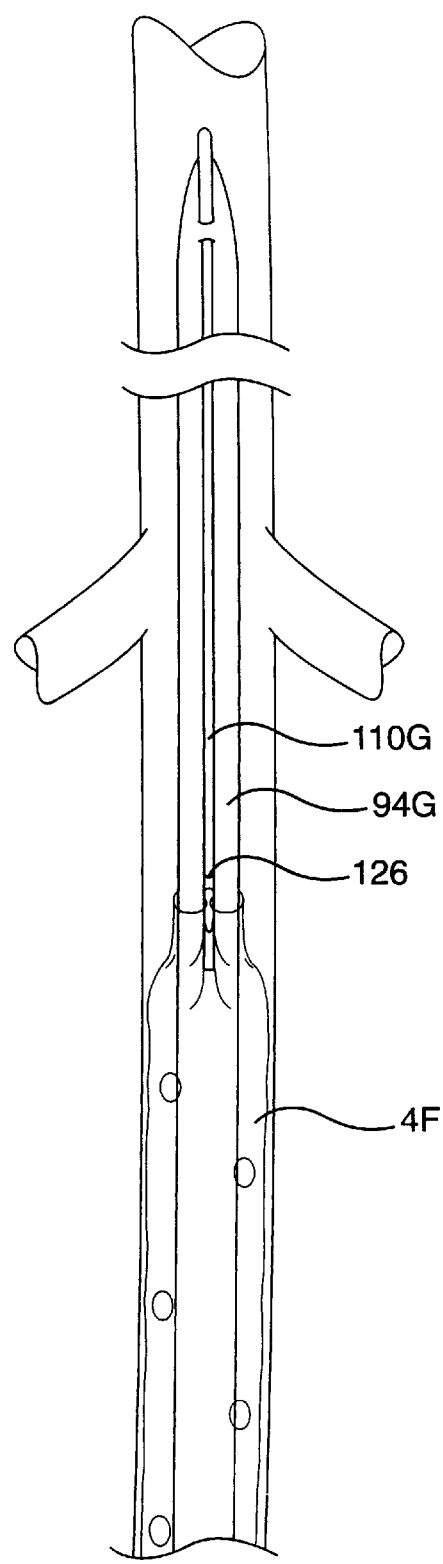
FIG. 26 shows the introducer of FIG. 24 with the expandable portion released from the channel.
Figure 25:
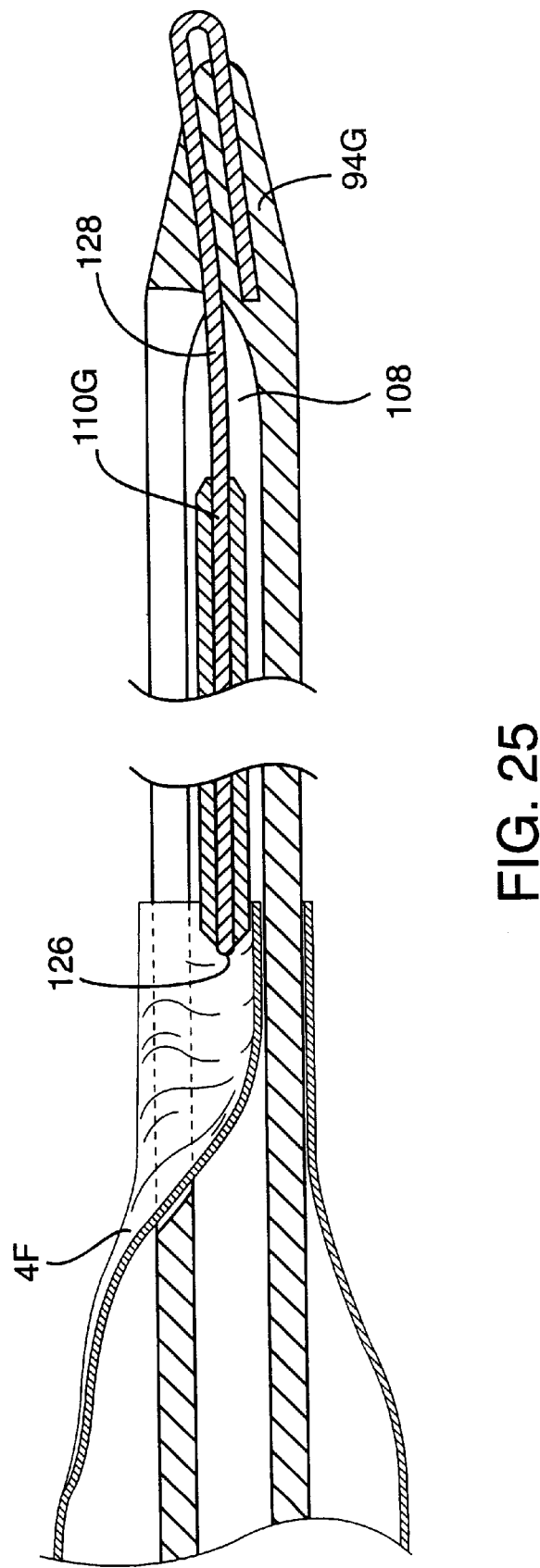
FIG. 25 is a cross-sectional view of the introducer of FIG. 24.

Turning now to FIGS. 24–26, another introducer 94G is disclosed wherein the retainer 110G is attached to the introducer 94G so that the retainer 110G does not require separation from the introducer 94G to deploy the expandable portion 4F. The retainer 110 is coupled to the introducer 94G at a location distal to channel 108 and extends proximally to a free end 126. The expandable portion 4F is mounted to the introducer 94G by sliding the distal end of the expandable portion 4F into the channel 108 below the free end 126. A spring 128 biases the retainer 110G toward the channel 108 to prevent inadvertent release of the expandable portion 4F. The spring 128 is a U-shaped clip having an end mounted to the introducer 94G and an opposite end mounted to the retainer 110G. The spring 128 may also be integrally formed with the retainer 110G and/or the introducer 94G.

In use, the introducer 94G is advanced into the patient's blood vessel in the manner described above. After the cannula 2 is advanced to the desired location, the introducer 94G is advanced as shown in FIG. 26. During this relative movement, the free end 126 of the retainer 110G moves beyond the distal end of the expandable portion 4F so that the expandable portion 4F is free to move out of the channel 108. The introducer 94G is then withdrawn and the cannula 2 may be used for introduction of the catheter 6 and/or infusion of fluids in the manner described above.

Figure 28:
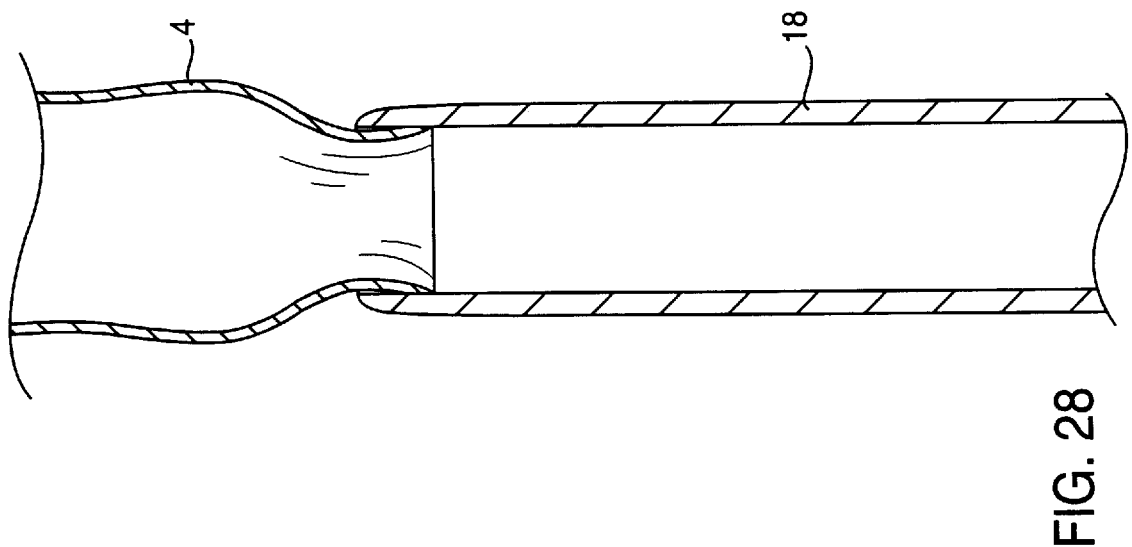
FIG. 28 shows the expandable portion of FIG. 27 everted to a position outside the tube.
Figure 27:
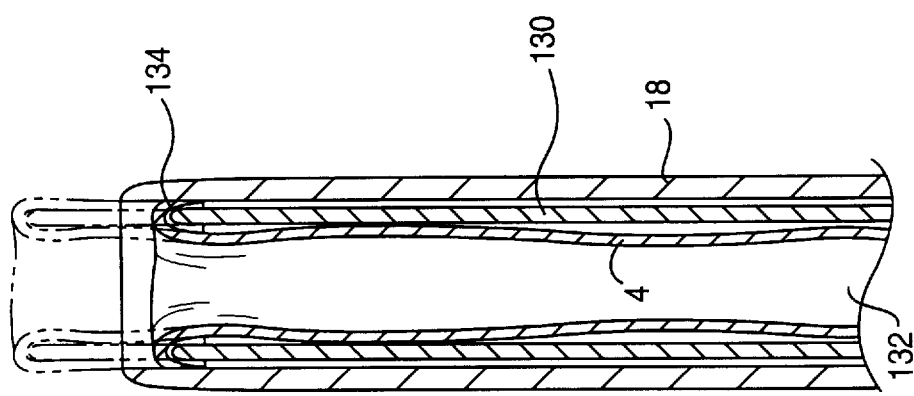
FIG. 27 shows another method of deploying the expandable portion with the expandable portion contained within the tube of the cannula.

Referring to FIGS. 27 and 28, another method of deploying the expandable portion 4 is shown. The expandable portion 4 is contained within the tube 18 when in the collapsed position as shown in FIG. 27 and is then everted outwardly to the expanded position of FIG. 28. The expandable portion 4 may be any of the expandable portions 4, 4A, 4B, 4D, 4E, 4F described herein. In the collapsed position, the expandable portion 4 is positioned in the tube 18 so that the expandable portion 4 does not interfere with insertion into the blood vessel. Once the tube 18 is in the patient, the expandable portion 4 is everted to the position of FIG. 28.

A tubular-shaped pusher 130 slides within the tube 118 to evert the expandable portion 4. The pusher 130 has a bore 132 which receives the expandable portion 4. As shown in phantom lines in FIG. 27, a distal end 134 of the pusher 130 slidably contacts the interior wall of the expandable portion 4 to evert expandable portion 4. An introducer (not shown) may be included for receipt in the bore 132 to facilitate introduction of the cannula 2.

Referring to FIGS. 29 and 30, yet another cannula 211 is shown which has an expandable portion 4H slidably received in the tube 18. A proximal end 136 of the expandable portion 4H seats against an inwardly tapered wall 138 of the tube 18. The proximal end 136 is configured to conform with the gradual inward taper of the tube 18 in a manner forming a hemostatic seal therewith. A ring 138 is embedded in the proximal end to provide additional strength and resiliency and prevent collapse of the proximal end. The ring 138 is also sized to provide sealed contact with the tube 18. The ring 138 is preferably made of a superelastic material, such as nitnol, but may also be made of any other suitable material. The expandable portion 4H is preferably moved distally with a pusher 140. The expandable portion 4H may be made of any of the suitable materials and may have any of the properties described herein.

Figure 32:
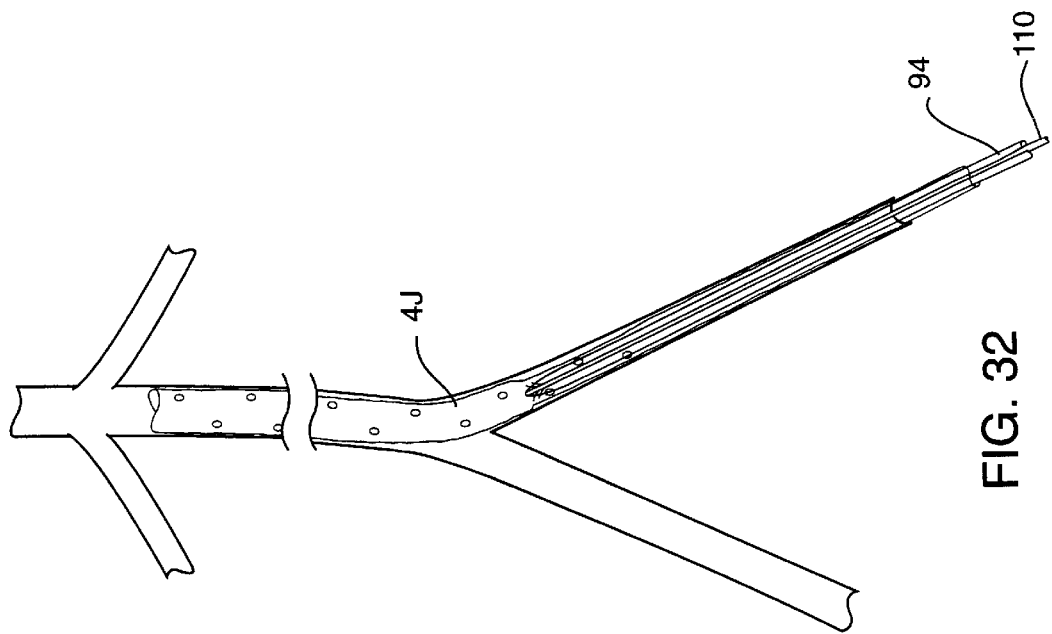
FIG. 32 shows the expandable portion of FIG. 31 with the introducer being withdrawn from the expandable portion.
Figure 31:
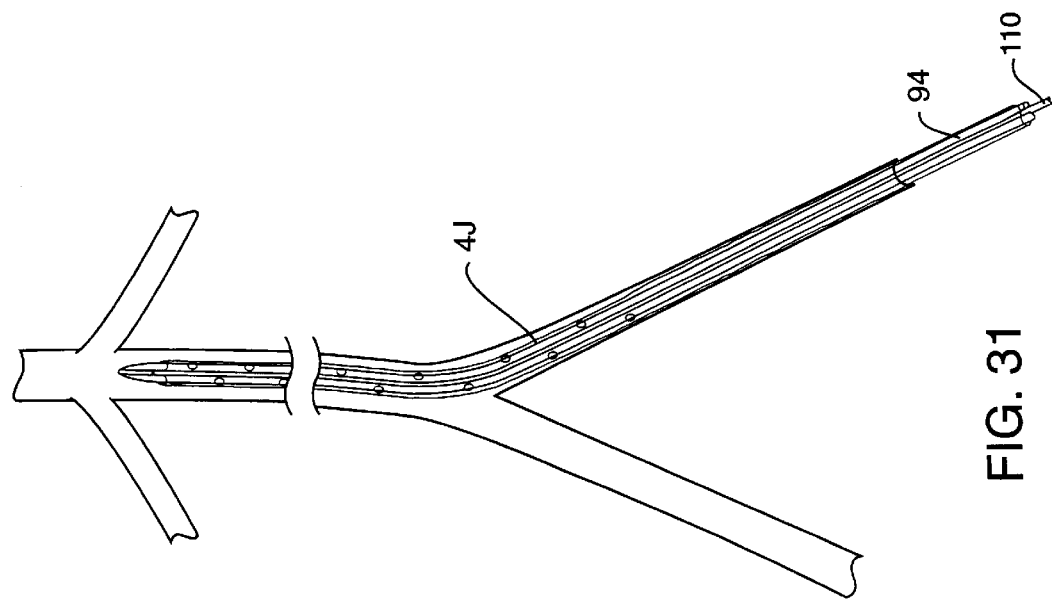
FIG. 31 shows another preferred expandable portion advanced into the blood vessel with the introducer.
Figure 33:
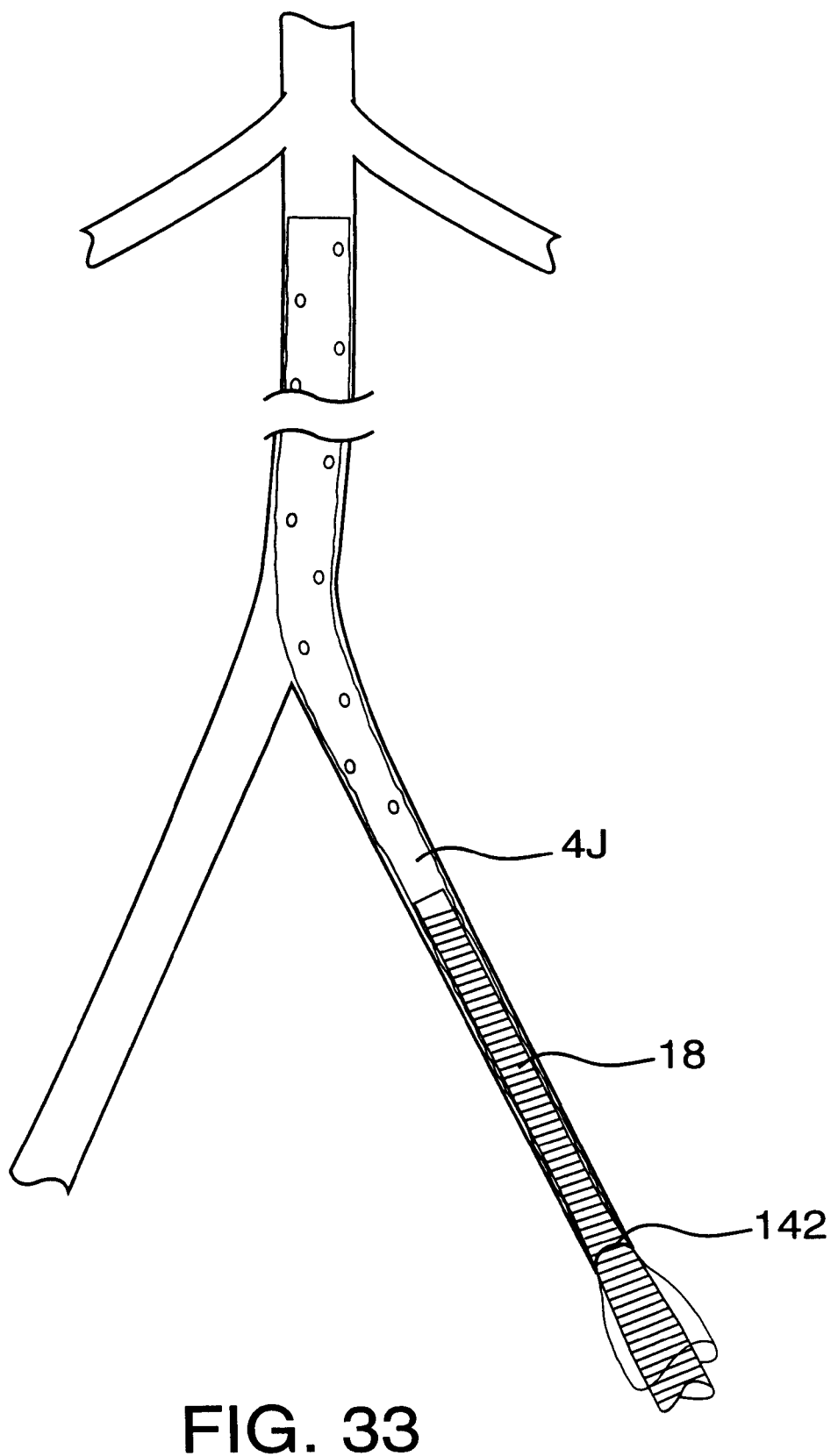
FIG. 33 shows the tube inserted into the expandable portion of FIG. 32.

Referring to FIGS. 31–33, another expandable portion 4J is shown with the expandable portion 4J being separated form the tube 18. Referring to FIG. 31, the expandable portion 4J is inserted into the blood vessel ahead of the tube 18 using the introducer 94 described above. The tube 18 is then inserted into the expandable portion 4J as shown in FIG. 33 and the introducer 94 and retainer 110 are removed. The tube 18 may be passed over the introducer 94 or the introducer 94 may be removed before inserting the tube 18 into the expandable portion 4J. A suture or an elastomeric ring 142 seals the space between the expandable portion 4J and tube 18. The expandable portion 4J advantageously protects the vessel during advancement of both the tube 18 and the catheter 6 (see FIG. 3). Furthermore, the tube 18 may be advanced relatively far into the vessel to prevent collapse of the expandable portion 4J without the risk of damaging the vessel with the tube 18 since the expandable portion 4J protects the vessel during advancement of the tube 18. The expandable portion 4J may then be used to receive the catheter 6 and/or for infusion of fluids, such as oxygenated blood, as described above.

We claim:

1. A method of performing a surgical procedure in a patient's vascular system, comprising the steps of:

providing a cannula having a fabric portion and a lumen, the fabric portion being formed from a plurality of interlaced fibers and being movable from a collapsed position to an expanded position;

inserting the fabric portion into a blood vessel of a patient in the collapsed position;

performing a surgical procedure through the lumen of the fabric portion with the fabric portion in the expanded position; and removing the fabric portion after the surgical procedure performing step.

2. The method of claim 1, wherein:

the surgical procedure performing step includes the step of passing a catheter through the lumen.

3. The method of claim 2, wherein:

the surgical procedure performing step is carried out with the catheter being an aortic occlusion catheter, the aortic occlusion catheter having a balloon configured to occlude the patient's ascending aorta.

4. The method of claim 1, wherein:

the surgical procedure performing step includes the step of passing a fluid through the lumen.

5. The method of claim 4, wherein:

the surgical procedure performing step is carried out with the fluid being oxygenated blood from a bypass system.

6. The method of claim 4, wherein:

the surgical procedure performing step is carried out with the fluid being infused through the lumen in a direction opposite to normal blood flow in a portion of the blood vessel in which the fabric portion is positioned.

7. The method of claim 1, wherein:

the providing step is carried out with the plurality of fibers forming a braided structure.

8. The method of claim 1, wherein:

the providing step is carried out with the plurality of fibers being at least 64 fibers.

9. The method of claim 1, wherein:

the providing step is carried out with the fabric portion having a porosity of at least 100 cubic centimeters of water per square centimeter of surface area per minute at 120 mm Hg.

10. The method of claim 1, wherein:

the providing step is carried out with the fabric portion having a porosity of at least 250 cubic centimeters of water per square centimeter of surface area per minute at 120 mm Hg.

11. The method of claim 1, wherein:

the providing step is carried out with the fabric portion having a porosity of at least 500 cubic centimeters of water per square centimeter of surface area per minute at 120 mm Hg.

12. The method of claim 1, wherein:

the providing step is carried out with at least some of the plurality of fibers being yarn.

13. The method of claim 12, wherein:

the providing step is carried out with the yarn having a denier between 150 and 600.

14. The method of claim 1, wherein:

the providing step is carried out with at least one of the plurality of fibers being a monofilament.

15. The method of claim 1, wherein:

the providing step is carried out with the monofilament being made of a material selected from the group consisting of polyester, polyethylene, polyolefin, polypropylene and polyurethane.

16. The method of claim 1, further comprising the steps of:

applying tensile force to the fabric portion during the surgical procedure step; and releasing the tensile force on the fabric portion after the surgical procedure step.

17. The method of claim 16, wherein:

the tensile force applying step reduces a diameter of fabric portion.

18. The method of claim 16, wherein:

the tensile force applying step is carried out with an introducer passing through the lumen of the fabric portion, the introducer extending beyond a distal end of the fabric portion, the introducer having a holder which holds a distal end of the fabric portion during the applying step; and the releasing step is carried out by separating the holder from the distal end of the fabric portion.

19. The method of claim 1, wherein:

the providing step is carried out with the fabric portion having a first outer dimension when in the collapsed condition and a second outer dimension when in the expanded condition, the second outer dimension being at least 25 percent larger than the first outer dimension.

20. The method of claim 19, wherein:

the providing step is carried out with the second outer dimension being at least 50 percent larger than the first outer dimension.

21. The method of claim 19, wherein:

the providing step is carried out with the first outer dimension being no more than 0.25 inch.

22. The method of claim 19, wherein:

the providing step is carried out with the second outer dimension being at least 0.35 inch.

23. A method of cannulating a patient's blood vessel, comprising the steps of:

providing a cannula having a tube and an expandable portion coupled to the tube, the expandable portion being movable from a collapsed condition to an expanded condition, a section of the expandable portion being contained within the tube when in the collapsed position and being movable to a position outside the tube when in the expanded position;

inserting the cannula into a patient's vascular system with the expandable portion being in the collapsed condition and the section being contained within the tube;

moving the section of the expandable portion to a position outside the tube; expanding the expandable portion to the expanded condition after the inserting step.

24. The method of claim 23 wherein:

the moving step is carried out by everting the section of the expandable portion.

25. The method of claim 23, wherein:

the moving step is carried out with the section of the expandable portion being slidably coupled to an interior surface of the tube.

\* \* \* \* \*